United States Patent
Friend et al.

Patent Number: 6,146,830
Date of Patent: Nov. 14, 2000

[54] METHOD FOR DETERMINING THE PRESENCE OF A NUMBER OF PRIMARY TARGETS OF A DRUG

[75] Inventors: Stephen H. Friend, Seattle, Wash.; Roland Stoughton, San Diego, Calif.

[73] Assignee: Rosetta Inpharmatics, Inc., Kirkland, Wash.

[21] Appl. No.: 09/159,352

[22] Filed: Sep. 23, 1998

[51] Int. Cl.$^7$ .............................. C12Q 1/68; C12Q 1/02; G01N 33/53

[52] U.S. Cl. ................. 435/6; 435/29; 435/7.1; 435/4; 436/501

[58] Field of Search .................. 435/6, 29, 4, 91.2, 435/7.1; 436/501

[56] References Cited

U.S. PATENT DOCUMENTS

| | | | |
|---|---|---|---|
| 5,510,270 | 4/1996 | Fodor et al. | 436/518 |
| 5,539,083 | 7/1996 | Cook et al. | |
| 5,556,752 | 9/1996 | Lockhart et al. | |
| 5,569,588 | 10/1996 | Ashby et al. | 435/6 |
| 5,578,832 | 11/1996 | Trulson et al. | |
| 5,965,352 | 10/1999 | Stoughton et al. | 435/4 |

FOREIGN PATENT DOCUMENTS

| | | |
|---|---|---|
| 0 534 858 A1 | 9/1992 | European Pat. Off. |
| WO 98/38329 A1 | 9/1998 | WIPO . |

OTHER PUBLICATIONS

Shupnik, M.A. et al. "Triiodothyronine regulation of thyrotropin subunit . . . " Endocrinology 118(1):367–371 1986.
DeRisi, J.L., et al. "Exploring metabolic and genetic control of gene exp . . . "Science 278:680–686 1997.
Lockhart, D.J., et al. "Expression monitoring by hybridization . . . "Nature Biotech 14 (13):1675–1680 1996.
Phillips, T.Y., et al. "O(log n) Bimodality analysis" Pattern Recognition 22(6):741–746 1989.
Blanchard AP and Hood L, "Sequence to array: probing the genome's secrets", Nat Biotechnol. Dec. 1996;14(13):1649.
Blanchard AP and Hood L, 1996, "High–density oligonucleotide arrays", Biosensors and Bioelectronics 11:687–690.
Brachmann CB et al., "Designer deletion strains derived from*Saccharomyces cerevisiae* S288C: a useful set of strains and plasmids for PCR–mediated gene disruption and other applications", Yeast. Jan. 30,; 1998 14(2):115–32.
Chirgwin et al., 1979, "Isolation of biologically active ribonucleic acid from sources enriched in ribonuclease", Biochemistry 18:5294–5299.
DeRisi et al., 1996, "Use of a cDNA microarray to analyse gene expression patterns in human cancer", Nat Genet 14:457–460.
Egholm et al., 1993, "PNA hybridizes to complementary oligonucleotides obeying the Watson–Crick hydrogen–bonding rules", Nature 365:566–568.
Ferguson et al., 1996, "A fiber–optic DNA biosensor microarray for the analysis of gene expression", Nature Biotechnol 14:1681–1684.

(List continued on next page.)

*Primary Examiner*—Stephanie Zitomer
*Assistant Examiner*—B.J. Forman
*Attorney, Agent, or Firm*—Pennie & Edmonds LLP

[57] ABSTRACT

This invention relates to methods and systems for characterizing the actions of drugs in cells. In particular, the invention provides methods for determining the presence of a number of primary targets through which a drug, drug candidate, or other compound of interest acts on a cell. Thus, the invention also relates to methods for drug development based on the disclosed methods for determining the presence of a number of primary targets of a drug. The methods of the invention involve: (i) measuring responses of cellular constituents to graded exposures of the cell to a drug of interest; (ii) identifying an "inflection concentration" of the drug for each cellular constituent measured; and (iii) identifying "expression sets" of cellular constituents from the distribution of the inflection drug concentrations. Each expression set corresponds to a particular primary target of the drug. The invention also provides computer systems which determine the presence of a number of targets of a drug by executing the disclosed methods.

31 Claims, 14 Drawing Sheets

OTHER PUBLICATIONS

Fodor et al., 1991, "Light–directed. spatially addressable parallel chemical synthesis", Science 251:767–773.

Froehler et al., 1986, "Synthesis of DNA via deoxynucleoside H–phosphonate intermediates", Nucleic Acids Res 14:5399–5407.

Gari et al., 1997, "A set of vectors with a tetracycline–regulatable promoter system for modulated gene expression in *Saccharomyces cerevisiae*", Yeast 13:837–848.

Goffeau et al., 1996, "Life with 6000 genes", Science 274:546, 563–567.

Jones JS et al., "Yeast *Saccharomyces cerevisiae* selectable markers in pUC18 polylinkers", Yeast. 1990 Sep.–Oct.;6(5):363–6.

Lander, 1996, "The new genomics: global views of biology", Science 274:536–539.

Lockhart et al., 1996, "Expression monitoring by hybridization to high–density oligonucleotide arrays", Nat Biotechnol 14:1675–1680.

Maskos and Southern, 1992, "Oligonucleotide hybridizations on glass supports: a novel linker for oligonucleotide synthesis and hybridization properties of oligonucleotides synthesised in situ", Nucleic Acids Res 20:1679–1684.

McBride and Caruthers, 1983, "An investigation of several deoxynucleoside phosphoramidites useful for synthesizing deoxyoligonucleotides", Tetrahedron Lett 24:245–248.

Nguyen et al., 1995, "Differential gene expression in the murine thymus assayed by quantitative hybridization of arrayed cDNA clones", Genomics 29:207–216.

Oliff et al., 1997, "Molecular Targets for Drug Development" in *Cancer: Principles and Practice of Oncology, Fifth Edition*, DeVita et al. (eds.), Lippincott–Raven Publishers, Philadelphia, Pa.

Pease et al., 1994, "Light–generated oligonucleotide arrays for rapid DNA sequence analysis", Proc Natl Acad Sci USA 91:5022–5026.

Phillips TY et al., "O(log n) Bimodality Analysis", Pattern Recognition 22:741–746. 1989.

Prashar and Weissman, 1996, "Analysis of differential gene expression by display of 3' end restriction fragments of cDNAs", Proc Natl Acad Sci USA 93:659–663.

Sagliocco et al., 1996, "Identification of proteins of the yeast protein map using genetically manipulated strains and peptide–mass fingerprinting", Yeast 12:1519–1533.

Schena et al., 1996, "Parallel human genome analysis: microarray–based expression monitoring of 1000 genes", Proc Natl Acad Sci USA 93:10614–10619.

Schena et al., 1995, "Quantitative monitoring of gene expression patterns with a complementary DNA microarray", Science 270:467–470.

Shalon et al., 1996, "A DNA microarray system for analyzing complex DNA samples using two–color fluorescent probe hybridization", Genome Res 6:639–645.

Shevchenko et al., 1996, "Linking genome and proteome by mass spectrometry: large–scale identification of yeast proteins from two dimensional gels", Proc Natl Acad Sci USA 93:14440–14445.

Velculescu, 1995, "Serial analysis of gene expression", Science 270:484–487.

Wach et al., 1994, "New heterologous modules for classical or PCR–based gene disruptions in *Saccharomyces cerevisiae,* " Yeast, 10:1793–808.

Heller et al., 1997, "Discovery and Analysis of Inflammatory Disease–Related Genes Using cDNA Microarrays," Proc. Natl. Acad. Sci. USA 94:2150–2155.

METHOD FOR DETERMINING THE PRESENCE OF A NUMBER OF PRIMARY TARGETS OF A DRUG

TABLE OF CONTENTS
1. FIELD OF THE INVENTION
2. BACKGROUND
3. SUMMARY OF THE INVENTION
4. BRIEF DESCRIPTION OF THE FIGURES
5. DETAILED DESCRIPTION
   5.1. INTRODUCTION
      5.1.1. DRUG ACTION AND BIOLOGICAL STATE
      5.1.2. BIOLOGICAL PATHWAYS
   5.2. OVERVIEW OF THE METHODS OF THE INVENTION
   5.3. ANALYTIC EMBODIMENTS
      5.3.1. DRUG RESPONSE REPRESENTATION
      5.3.2. INFLECTION DRUG CONCENTRATION
      5.3.3. STATISTICAL ANALYSIS
      5.3.4. IMPLEMENTATION SYSTEMS AND METHODS
   5.4. MEASUREMENT METHODS
      5.4.1. MEASUREMENT OF DRUG RESPONSE DATA
      5.4.2. TRANSCRIPTIONAL STATE MEASUREMENT
         5.4.2.1. MICROARRAYS GENERALLY
         5.4.2.2. PREPARING PROBES FOR MICROARRAYS
         5.4.2.3. ATTACHING PROBES TO THE SOLID SURFACE
         5.4.2.4. TARGET POLYNUCLEOTIDE MOLECULES
         5.4.2.5. HYBRIDIZATION TO MICROARRAY
         5.4.2.6. SIGNAL DETECTION AND DATA ANALYSIS
         5.4.2.7. OTHER METHODS OF TRANSCRIPTIONAL STATE MEASUREMENT
      5.4.3. MEASUREMENTS OF OTHER ASPECTS OF BIOLOGICAL STATE
         5.4.3.1. TRANSLATIONAL STATE MEASUREMENTS
         5.4.3.2. ACTIVITY STATE MEASUREMENTS
         5.4.3.3. MIXED ASPECTS OF BIOLOGICAL STATE
6. EXAMPLES
   6.1. IDENTIFICATION OF DUAL PRIMARY TARGETS
   6.2. IDENTIFICATION OF A SINGLE PRIMARY TARGET
   6.3. ASSESSING THE CONFIDENCE LEVEL OF BIMODALITY
7. REFERENCES CITED

1. FIELD OF THE INVENTION

The field of this invention relates to methods and systems for characterizing the action of drugs in cells. In particular, the methods and systems of the invention relate to determining whether a drug, drug candidate, or some other compound of interest is altering multiple primary targets in a cell, as well as application of these methods to drug discovery.

2. BACKGROUND

The identification of the multiple primary targets of a drug or drug candidate is a problem of great importance in the process of drug discovery. In particular, one of the major difficulties in drug discovery is the identification of compounds that have selective actions on specific primary targets.

Two approaches presently dominate the search for new drugs. The first begins with a screen for compounds that have a desired effect on a cell (e.g., induction of apoptosis), or organism (e.g., inhibition of angiogenesis) as measured in a specific biological assay. Compounds with the desired activity may then be modified to increase potency, stability, or other properties, and the modified compounds retested in the assay. Thus, a compound that acts as an inhibitor of angiogenesis when tested in a mouse tumor model may be identified, and structurally related compounds synthesized and tested in the same assay. A critical limitation of this approach is that, often, the mechanisms of action, such as the molecular target(s) and cellular pathway(s) affected by the compound, are unknown, and cannot be determined by the screen. Further, the addition may provide little information about the specificity, either in terms of target or pathways, of the drug's effect. In contrast, the second approach to drug screening involves testing numerous compounds for a specific effect on a known molecular target, typically a cloned gene sequence of an isolated enzyme or protein. For example, high-throughput assays can be developed in which numerous compounds can be tested for the ability to change the level of transcription from a specific promoter or the binding of identified proteins.

The use of high-throughput screens is a powerful methodology for identifying drug candidates, however, it has limitations. In particular, the assay provides little or no information about the effects of a compound at the cellular or organismal level. In order to develop lead compounds into successful drugs, it is necessary not only to find compounds which are able to bind well to the primary target which is being screened, but also to insure that the compounds are not simultaneously interacting with other targets within the cell. These effects must be tested by using the drug in a series of cell biologic and whole animal studies to determine toxicity of side effects in vivo. In fact, analysis of the specificity and toxicity studies of candidate drugs can consume a significant fraction of the drug development process (see, e.g., Oliff et al., 1997, "Molecular Targets for Drug Development," in DeVita et al., *Cancer: Principles & Practice of Oncology*, 5th Ed., Lippincott-Raven Publishers, Philadelphia, Pa.).

Several gene expression assays are now becoming practicable for quantitating the drug effect on a large fraction of the genes and proteins in a cell culture (see, e.g., Schena et al., 1995, *Science* 270:467–470; Lockhort et al., 1996, *Nature Biotechnology* 14:1675–1680; Blanchard et al., 1996, *Nature Biotechnology* 14:1649; Ashby et al., U.S. Pat. No. 5,569,588, issued Oct. 29, 1996). Raw data from these gene expression assays are often difficult to coherently interpret. Such measurement technologies typically return numerous genes with altered expression in response to a drug, typically 50–100, possibly up to 1,000 or as few as 10. In the typical case, without more analysis, it is not possible to discern cause and effect from such data alone. The fact that one or a few genes among many has an altered expression in a pair of related biological states yields little or no insight into what caused this change and what the effects of this change are. These data in themselves do not inform an investigator about the pathways affected or primary targets of a drug. They do not indicate which effects result from affects on one particular primary target (e.g., the target screened in a high-throughput assay) versus which effects are the result of other primary targets of the drug.

Knowledge of all the primary targets is necessary in understanding efficacy, side-effects, toxicities, possible failures of efficacy, activation of metabolic responses, etc. Further, the identification of all primary targets of a drug can lead to discovery of alternate primary targets suitable to achieve the original therapeutic response. However, without effective methods of analysis, one is left to ad hoc further experimentation to interpret such gene expression results in terms of biological pathways and mechanisms. Systematic procedures for guiding the interpretation of such data and or such experimentation are needed.

Thus, there is a need for improved (e.g., faster and less expensive) systems and methods to identify multiple primary targets in a cell, based on effective interpretation of such data as gene expression data.

Discussion or citation of a reference herein shall not be construed as an admission that such reference is prior art to the present invention.

3. SUMMARY OF THE INVENTION

The present invention relates to methods and systems for testing and confirming the number of primary targets through which a drug or other compound of interest acts on a cell. The invention also relates to methods and systems for identifying the proteins and genes which are affected by each primary target of a drug or other compound of interest. Further, the invention also relates to methods for drug development based on the methods for testing and confirming the number of primary targets through which a drug or drug candidate acts on a cell.

The principles of the methods of the invention involve analyzing measurements of cellular constituents, such as RNA or protein abundances or activities, in response to varying strengths of drug exposure. The responses are analyzed to determine, for each individual measured cellular constituent, a drug concentration at which the individual cellular constituent is said to be activated (i.e., increased in expression or activity), or de-activated (i.e., decreased in expression or activity). The distribution of the so determined drug concentrations is then analyzed to identify clusters or sets of cellular constituents that are activated at a specific drug concentration. Because a drug will generally have different potencies against different primary targets, the identification of such "expression sets" of cellular constituents is the key element that identifies the existence of primary targets of a drug or compound of interest.

The invention is based, at least in part, on the discovery that individual primary targets of a drug engage in multiple secondary and tertiary gene expression changes which form coherent "expression sets". These coherent expression sets are activated or de-activated at specific concentrations of a drug. Thus, the individual primary targets of a drug can be identified, according to the methods of the present invention, by identifying individual expression sets which are activated (or de-activated) at specific drug concentrations. The methods do not require the identification of the individual components in a drug pathway or pathways, e.g., using genetic or drug phenotypes. Rather, expression sets corresponding to individual primary targets of a drug can be identified through simple analysis of RNA or protein abundances or activities at varying strengths of drug exposure.

The present invention overcomes the limitations in the prior art by providing methods of identifying multiple primary targets of a drug in a cell. Thus, the methods of the invention are useful, e.g., in drug discovery or drug screening, to identify not only compounds which have high affinity for a particular primary target, but also to insure that the compounds are not simultaneously interacting with other targets within the cell. In more detail, the present invention provides methods and systems for identifying one or more primary targets of a drug in a cell by: (i) measuring responses of cellular constituents to graded exposures of the cell to a drug of interest; (ii) identifying a "inflection concentration" of the drug for each cellular constituent measured; and (iii) identifying "expression sets" of cellular constituents from the distribution of the inflection drug concentrations. The number of primary targets of the drug is simply the number of expression sets identified.

In various embodiments, the responses of cellular constituents can be measured by measuring gene expression (i.e., RNA levels), protein abundances, protein activities, or a combination of such measurements. In various embodiments the inflection concentration may be determined from the maximum (or minimum) slope of the cellular constituent's response to graded exposure to the drug, or, alternatively, the drug exposure at which the response is one-half its asymptotic value.

In a first embodiment, the present invention provides a method for identifying one or more primary targets of a drug in a cell type, the method comprising identifying one or more expression sets wherein: (a) the expression sets each comprise a plurality of cellular constituents, each cellular constituent having an inflection concentration associated with the drug; (b) the inflection concentration of a cellular constituent is determined by the particular level of exposure to the drug at which the cellular constituent is activated or deactivated by the drug in a drug response; and (c) the drug response is provided by a method comprising measuring the pluralities of cellular constituents in a cell of said cell type at a plurality of levels of exposure to the drug. Each expression set corresponds to a primary target of the drug. In various aspects of the first embodiment, the inflection concentration of a cellular constituent may be, e.g., the level of exposure to the drug wherein the absolute slope of the drug response of the cellular constituent is maximum, or, alternatively, the level of exposure to the drug wherein the drug response of the cellular constituent is one-half its asymptotic value. In various aspects of the first embodiment, the expression sets are identified from the distribution or histogram of the inflection concentrations of the pluralities of cellular constituents wherein each of the expression sets corresponds to a mode in the histogram. The modes in the histogram may be identified, for example, by visual inspection of the histogram, or by an objective statistical test. In on particular aspect of the first embodiment, the objective statistical test is a statistical test based on the Fisher Distance.

The present invention also provides, in a second embodiment, methods for identifying one or more primary targets of a change in the physical environment of a cell type according to the method described above for the first embodiment of the invention.

In another embodiment, the present invention provides methods for comparing the mode or modes of action of two or more drug or drug compositions. The methods of this embodiment involve identifying the primary targets of each drug or drug compositions according to the methods of the first embodiment, and comparing the primary targets thus identified for each drug or drug compositions. In one particular aspect of this embodiment, the two or more drug or drug compositions include different compositions of the same drug.

In yet another embodiment, the invention provides a computer system for identifying one or more primary targets.

The computer system of this embodiment of the invention comprises: (a) a processor, (b) a memory coupled to the processor, and (c) one or more programs encoded by the memory. The one or more programs encoded by the memory cause the processor to identify one or more expression sets wherein: (i) the expression sets each comprise a plurality of cellular constituents, each cellular constituent having an inflection concentration associated with the drug; (ii) the inflection concentration of a cellular constituent is determined by the particular level of exposure to the drug at which the cellular constituent is activated or deactivated by the drug in a drug response; and (iii) the drug response is provided by a method comprising measuring the pluralities of cellular constituents in a cell of said cell type at a plurality of levels of exposure to the drug. Each expression set thereby identified by the processor corresponds to a primary target of the drug. In various aspects of this second embodiment, the inflection concentrations may be made available in the memory of the computer system, e.g., may be loaded into the memory by a user. In various aspects of the second embodiment, the response profile may be made available in the memory of the computer system, e.g., may be loaded into the memory by a user. In a particular embodiment, the programs of the computer system further cause the processor to determine the inflection concentrations from the drug response made available in the memory.

4. BRIEF DESCRIPTION OF THE FIGURES

Figure 6:
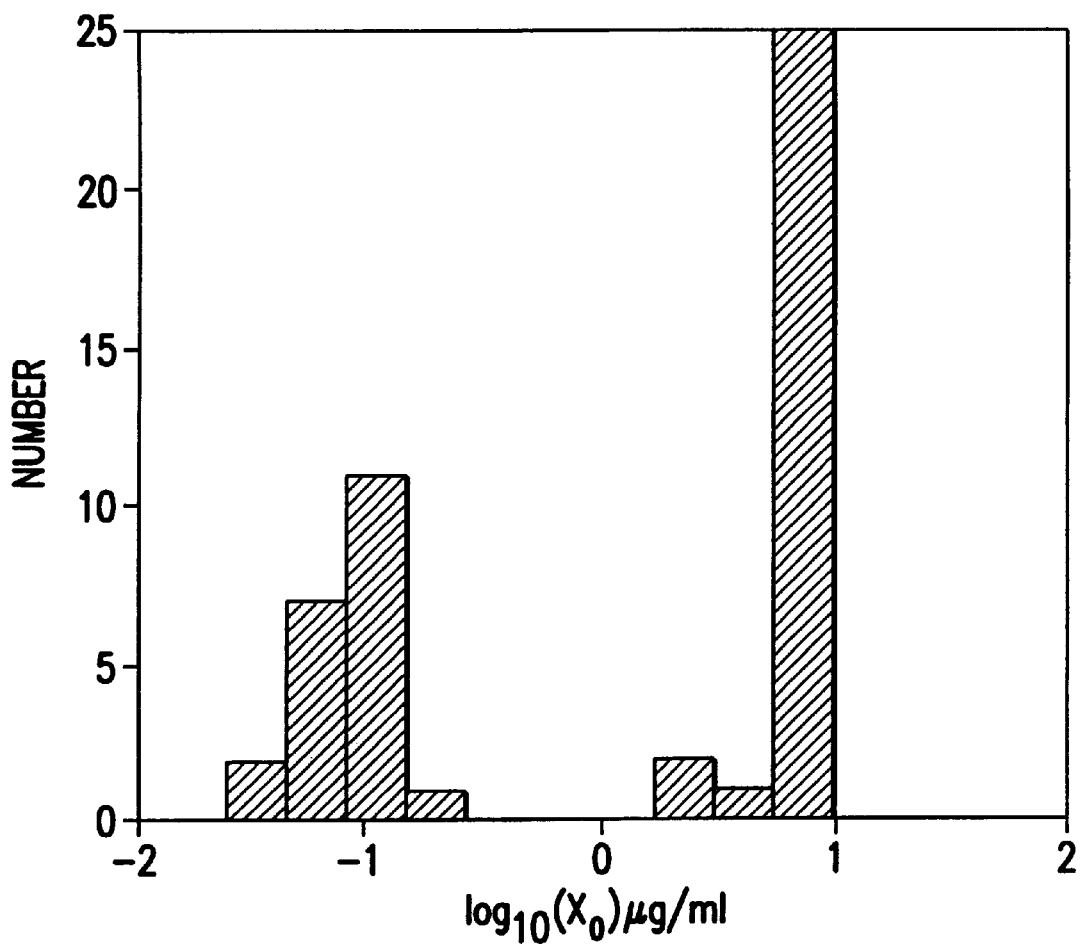
FIG. 6 illustrates the distribution of inflection concentrations $x_0$ obtained from fitting a Hill function to the responses illustrated in FIG. 4; the distribution of inflection concentrations is distinctly bimodal.
Figure 12A:
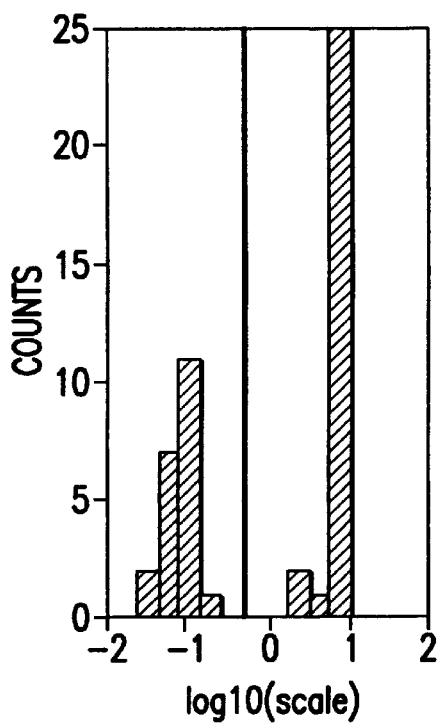
Figure 12B:
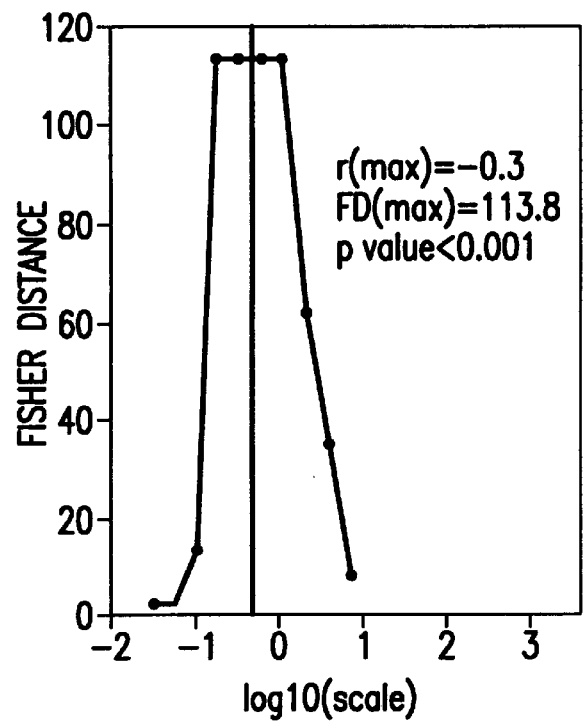

FIG. 12 shows the calculation of the maximum Fisher Distance $FD_{max}$ for the histogram shown in FIG. 6 for the FK506 drug titration experiments; FIG. 12A shows the histogram of FIG. 6 with a vertical line marking the value of the partition location $\gamma$ at which the Fisher Distance has a maximum; FIG. 12B is a plot of the Fisher Distance vs. $\gamma$.

Figure 13A:
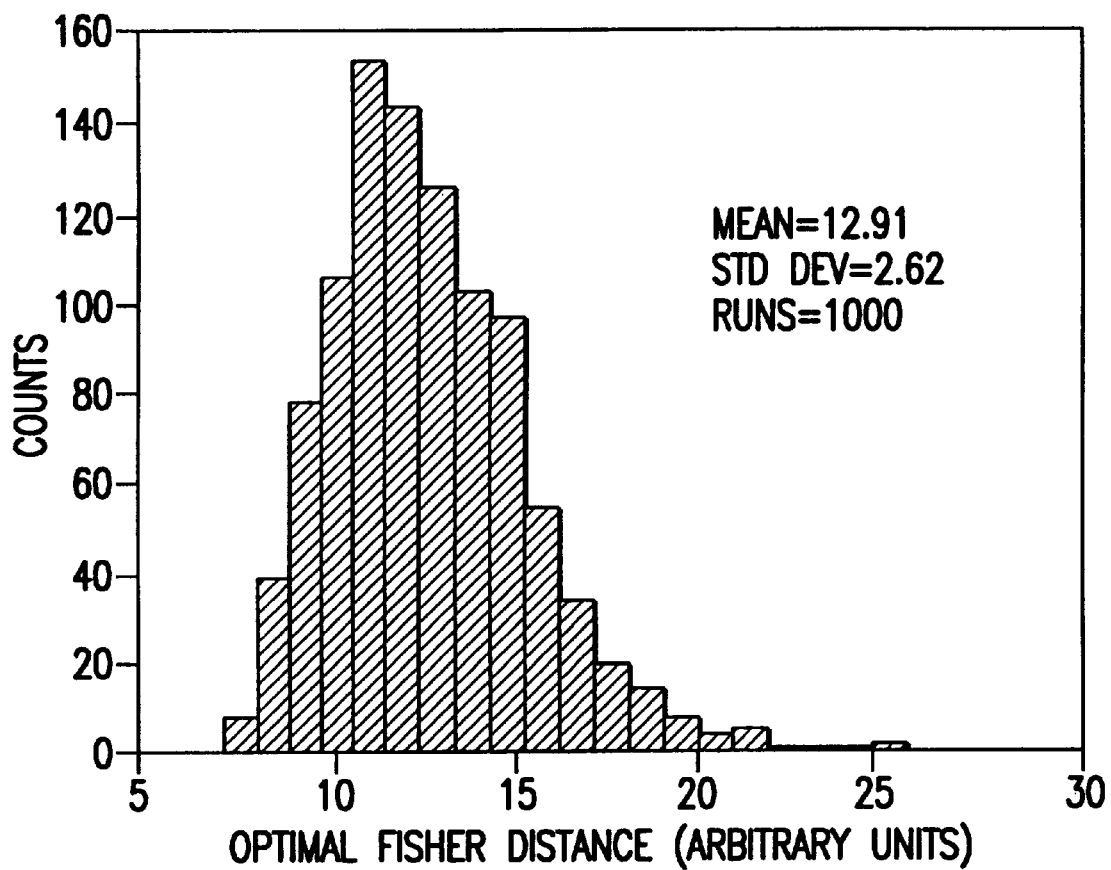
Figure 13B:
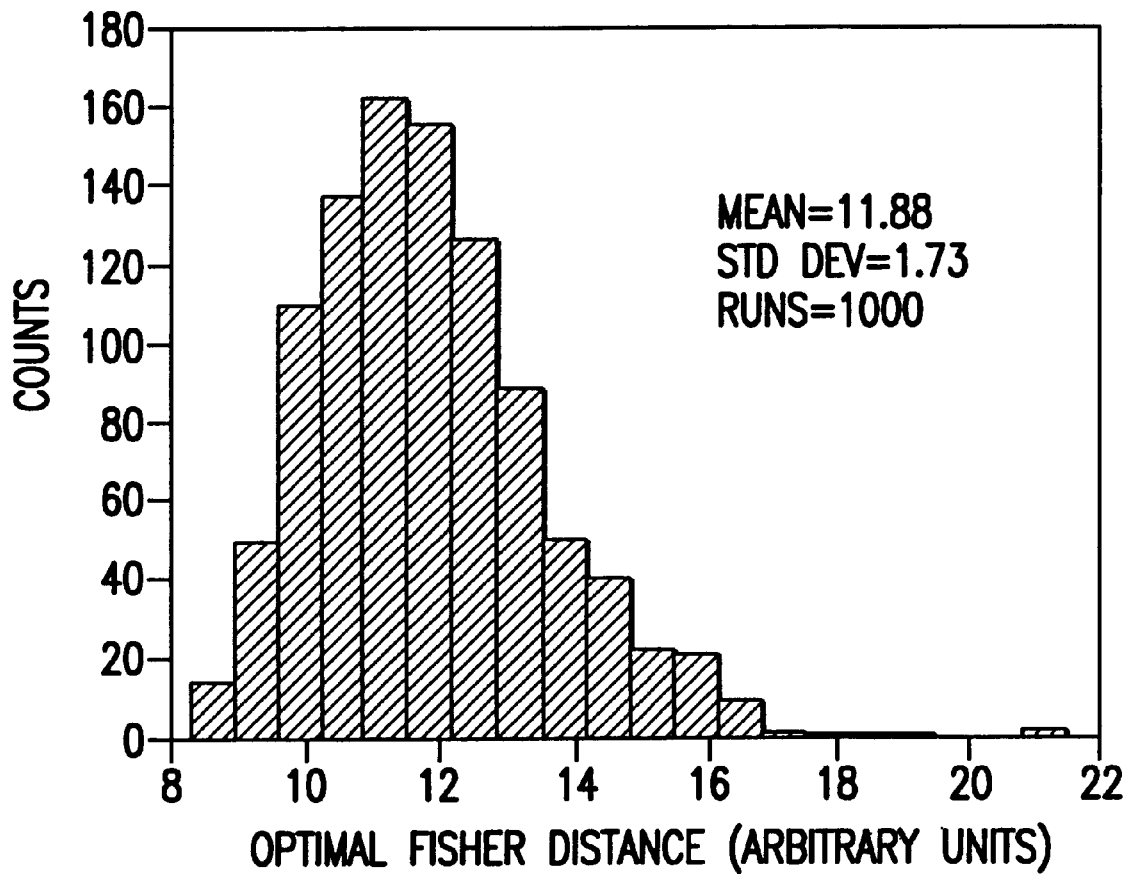

FIG. 13 shows distributions of maximum Fisher Distance statistic for Monte Carlo realizations of the unimodal distribution of inflection drug concentrations; FIG. 13A shows the distribution of maximum Fisher Distance statistic for Monte Carlo realizations of a uniform distribution; FIG. 13B shows the distribution of maximum Fisher Distance statistic for Monte Carlo realizations of a triangle distribution (i.e., ramping from zero at the left most bin to an arbitrary maximum at the right).

Figure 8:
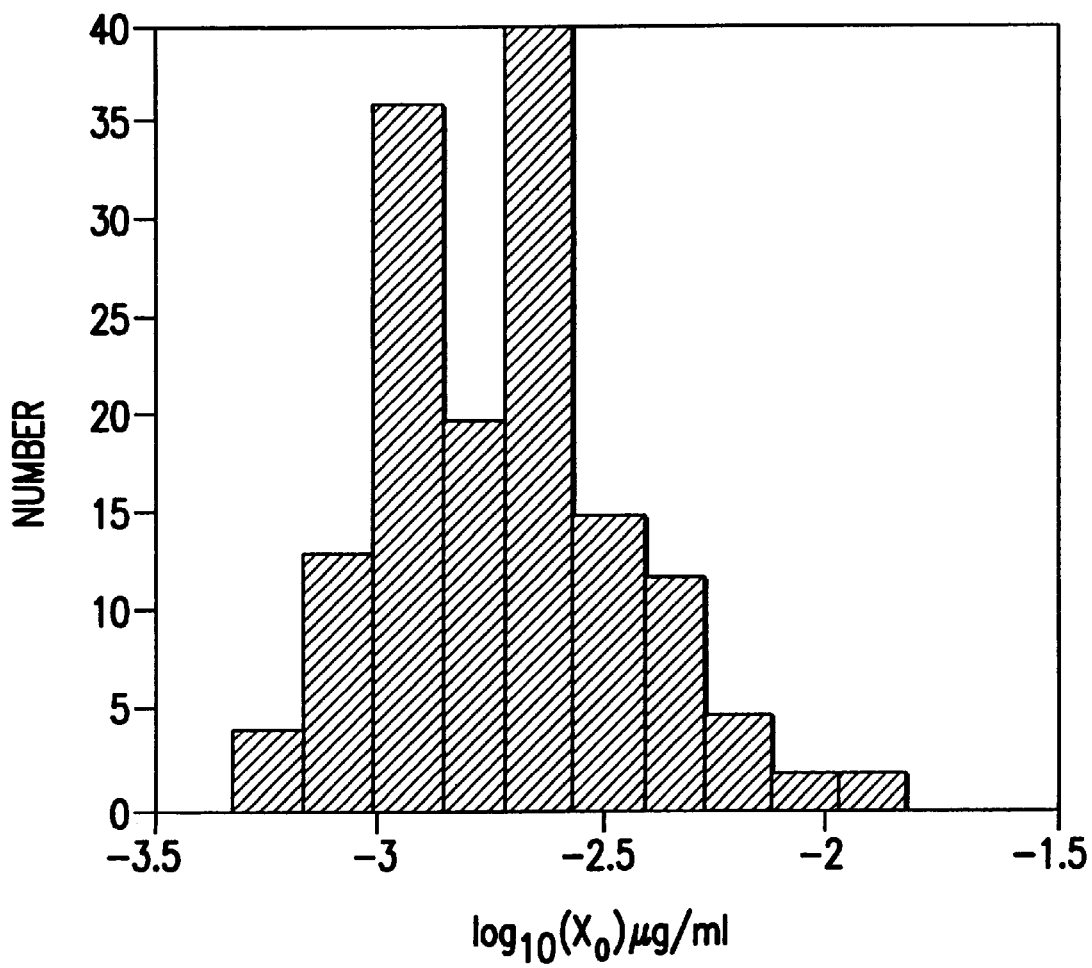
FIG. 8 illustrates the unimodal distribution of inflection concentrations $x_0$ obtained from fitting a Hill function to the response illustrated in FIG. 7.
Figure 14A:
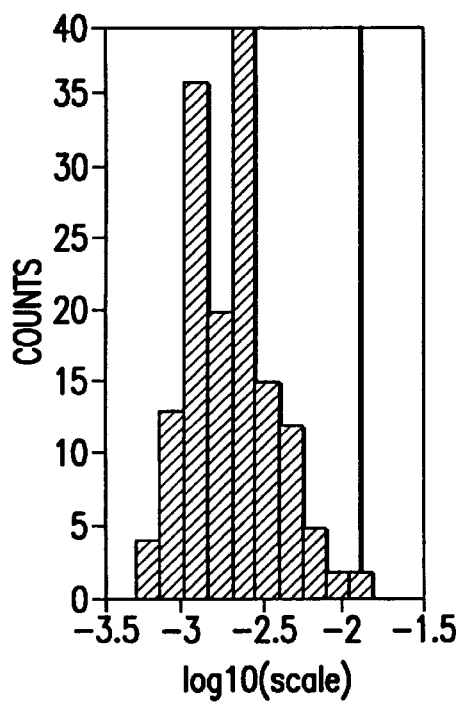
Figure 14B:
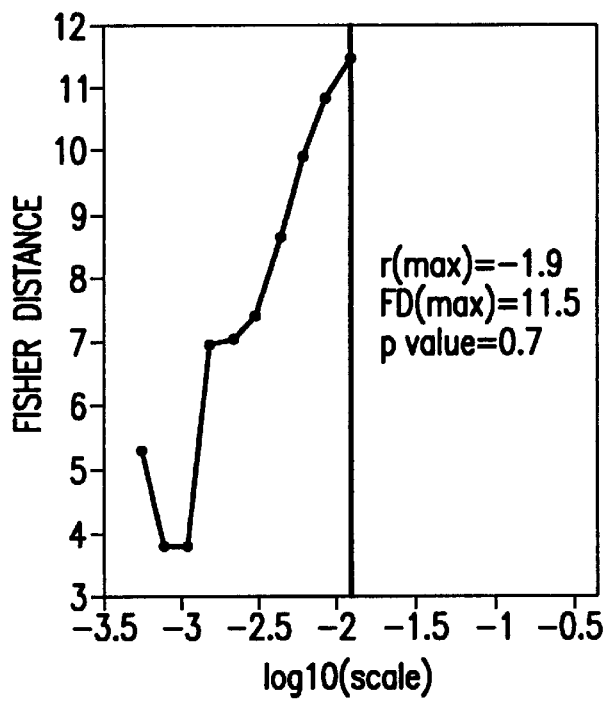

FIG. 14 shows the calculation of the maximum Fisher Distance $FD_{max}$ for the histogram shown in FIG. 8 for the specific ERG11 protein perturbation experiments; FIG. 14A shows the histogram of FIG. 8 with a vertical line marking the value of the partition location $\gamma$ at which the Fisher Distance has a maximum; FIG. 14B is a plot of the Fisher Distance vs. $\gamma$.

5. DETAILED DESCRIPTION

This section presents a detailed description of the invention and its application to drug discovery. This description is by way of several exemplary illustrations, in increasing detail and specificity, of the general methods of this invention. These examples are non-limiting, and related variants that will be apparent to one of skill in the art are intended to be encompassed by the appended claims. Following these examples are descriptions of specific embodiments of the data gathering steps that accompany the general methods.

5.1. Introduction

The present invention relates to methods and systems for identifying one or more primary targets of a drug, a drug candidate, or other compound of interest in a cell. In particular, the methods and systems of the invention enable one to determine the number of primary targets altered by a drug in a cell. These methods involve analyzing measurements of changes in the biological state of a cell in a response to graded levels of drug exposure to determine, for each cellular constituent, a drug concentration at which the cellular constituent is said to be activated or deactivated. The distribution of these "inflection drug concentrations", and, in particular, the modality (i.e., unimodal, bimodal, trimodal, etc.) of the distribution determined the number of primary targets affected by the drug in the cell.

This section first presents certain preliminary concepts including those of drug action, of the biological state of a cell, and of biological pathways, which, according to this invention, represent drug action in a cell. Next, a schematic and non-limiting overview of the methods of this invention is presented. The following sections present the methods of this invention in greater detail.

Although, for simplicity this disclosure often makes reference to single cells (e.g., "RNA is isolated from a cell perturbed at a single gene"), it will be understood by those of skill in the art that more often any particular step of the invention will be carried out using a plurality of genetically similar cells, e.g., from a cultured cell line. Such similar cells are called herein a "cell type". Such cells are either from naturally single celled organisms, or are derived from multi-cellular higher organisms.

In particular, Section 5.1 describes certain preliminary concepts useful in the further description of this invention. Section 5.2 generally describes the methods of the invention. Section 5.3 describes a preferred analytic embodiment of the methods of the invention. Section 5.4 describes methods of measuring cellular constituents.

5.1.1. Drug Action and Biological State

According to the current invention, drugs are any compounds of any degree of complexity that perturb a biological system, whether by known or unknown mechanisms and whether or not they are used therapeutically. Drugs thus include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; pesticides; herbicides; insecticides; and so forth. The biological effect of a drug may be a consequence of, inter alia, drug-mediated changes in the rate of transcription or degradation of one or more species of RNA, the rate or extent of translation or post-translational processing of one or more polypeptides, the rate or extent of the degradation of one or more proteins, the inhibition or stimulation of the action or activity of one or more proteins, and so forth. In fact, most drugs exert their affects by interacting with a protein. Drugs that increase rates or stimulate activities or levels of a protein are called herein "activating drugs", while drugs that decrease rates or inhibit activities or levels of a protein are called herein "inhibiting drugs". As will be clear to the skilled artisan, while the invention is described herein in terms of identifying the primary targets of a "drug," it is equally applicable to identifying the primary targets of a particular composition which comprises or contains a drug, but which may vary in its targets from a different composition containing the same drug but different additional ingredients.

The methods of identifying primary targets of a drug or drugs in a cell can be used, e.g., to determine therapeutic efficacy (e.g., if one or more particular therapeutic cellular constituents are primary drug targets); to determine potentials for side effects and/or toxicity (e.g., if other primary drug targets exists); and to compare the mode or modes of drug action for two or more different drugs or drug compositions by testing whether identical modes of action exist or not, as may be example, for example, during the ANDA process. In the last aspect, different drugs may include, e.g., different compositions or preparations of the same pharmacophore.

In addition to drugs, this invention is equally applicable to those changes in the aspects of the physical environment that perturb a biological system in targeted manners. Such environmental changes can include moderate changes of temperature (e.g., a temperature elevation of 10° C.) or exposure to moderate doses of radiation. Other environmental aspects include the nutritional environment, such as the presence of only particular sugars, amino acids, and so forth.

The biological effects of a drug (or a physical environmental change) are measured in the instant invention by observations of changes in the biological state of a cell. The cell may be of any type, e.g., prokaryotic, eukaryotic, mammalian, plant, or animal. The biological state of a cell, as used herein, is taken to mean the state of a collection of cellular constituents, which are sufficient to characterize the cell for an intended purpose, such as for characterizing the effects of a drug. The measurements and/or observations made on the state of these constituents can be of their abundances (i.e., amounts or concentrations in a cell), or their activities, or their states of modification (e.g., phosphorylation), or other measurements relevant to the characterization of drug action. In various embodiments, this invention includes making such measurements and/or observations on different collections of cellular constituents. These different collections of cellular constituents are also called herein aspects of the biological state of the cell. As used herein, the term "cellular constituents" is not intended to refer to known subcellular organelles, such as mitochondria, lysozomes, etc.

One aspect of the biological state of a cell usefully measured in the present invention is its transcriptional state. The transcriptional state of a cell includes the identities and abundances of the constituent RNA species, especially mRNAs, in the cell under a given set of conditions. Preferably, a substantial fraction of all constituent RNA species in the cell are measured, but at least a sufficient fraction is measured to characterize the action of a drug of interest. The transcriptional state is the currently preferred aspect of the biological state measured in this invention. It can be conveniently determined by, e.g., measuring cDNA abundances by any of several existing gene expression technologies.

Another aspect of the biological state of a cell usefully measured in the present invention is its translational state. The translational state of a cell includes the identities and abundances of the constituent protein species in the cell under a given set of conditions. Preferably, a substantial fraction of all constituent protein species in the cell are measured, but at least, a sufficient fraction is measured to characterize the action of a drug of interest. As is known to those of skill in the art, the transcriptional state is often representative of the translational state.

Other aspects of the biological state of a cell are also of use in this invention. For example, the activity state of a cell, as that term is used herein, includes the activities of the constituent protein species (and optionally catalytically active nucleic acid species) in the cell under a given set of conditions. As is known to those of skill in the art, the translational state is often representative of the activity state.

The present invention is also adaptable, where relevant, to "mixed" aspects of the biological state of a cell in which measurements of different aspects of the biological state of a cell are combined. For example, in one mixed aspect, the abundances of certain RNA species and of certain protein species, are combined with measurements of the activities of certain other protein species. Further, it will be appreciated from the following that this invention is also adaptable to other aspects of the biological state of the cell that are measurable.

Drug exposure will typically affect many constituents of whatever aspects of the biological state of a cell are being measured and/or observed in a particular embodiment of the invention. For example, as a result of regulatory, homeostatic, and compensatory networks and systems known to be present in cells, even an "ideal drug," i.e., a drug that directly affects only a single constituent in a cell, and without direct effects on any other constituent, will have complicated and often unpredictable indirect effects. A drug that specifically and completely inhibits activity of a single hypothetical protein, protein P, is considered here as an example. Although the drug itself will directly change the activity of only protein P, additional cellular constituents that are inhibited or stimulated by protein P, or which are elevated or diminished to compensate for the loss of protein P activity will also be affected. Still other cellular constituents will be affected by changes in the levels or activity of the second tier constituents, and so on. Therefore, the direct effect of the drug on its target, protein P, is hidden in the large number of indirect effects downstream from protein P. Such downstream effects of protein P are called herein the biological pathway originating at protein P.

Accordingly, a "non-ideal" drug that directly affects more than one primary molecular target, may have still more complicated downstream effects. In one aspect, according to the present invention, the analysis of these effects provides considerable information about the drug including, for example, identification of biological pathways effected by the drug and which explain its action and side effects of toxicities in the cell. In a related aspect, the present invention provides methods for carrying out this analysis.

Measurement of the transcriptional state of a cell is preferred in this invention, not only because it is relatively easy to measure but also because, although a drug may act through a post-transcriptional mechanism (such as inhibition of the activity of a protein or change in its rate of degradation), the administration of a drug to a cell almost always results in a measurable change, through direct or indirect effects, in the transcriptional state. A reason that drug exposure changes the transcriptional state of a cell is because the previously mentioned feed back systems, or networks, which react in a compensatory manner to infections, genetic modifications, environmental changes (including drug administration), and so forth do so primarily by altering patterns of gene expression or transcription. As a result of internal compensations, many perturbations to a biological system, although having only a muted effect on the external behavior of the system, can nevertheless profoundly influence the internal response of individual elements, e.g., gene expression, in the cell.

5.1.2. Biological Pathways

Figure 1:
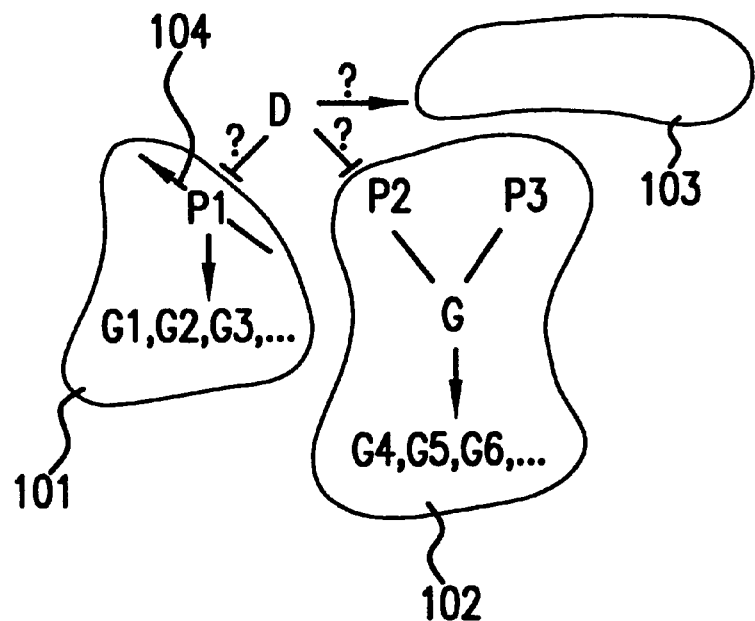
FIG. 1 illustrates exemplary pathways hypothesized for the action of a drug D on a biological system.

In the instant invention, drug effects on a cell, whether an ideal or non-ideal drug and however measured in a particular implementation, are represented by combining the effects of the drug on individual biological pathways. For example, FIG. 1 illustrates that drug D acts on a cell by interacting with biological pathways 101, 102, and 103 (details of pathway 103 are not illustrated). The arcs between drug D and these pathways represent possible action of drug D on these pathways. The entire action of drug D on the cell is assumed to be expressible as a combination of drug D's actions on one or more of these three pathways.

As used herein, a biological pathway is generally understood to be a collection of cellular constituents related in that each cellular constituent of the collection is influenced according to some biological mechanism by one or more other cellular constituents in the collection. The cellular constituents making up a particular pathway can be drawn from any aspect of the biological state of a cell, for example, from the transcriptional state, or the translational state, or the activity state, or mixed aspects of the biological state. Therefore, cellular constituents of a pathway can include mRNA levels, protein abundances, protein activities, degree of protein or nucleic acid modification (e.g., phosphorylation or methylation), combinations of these types of cellular constituents, and so forth. Each cellular constituent of the collection is influenced by at least one other cellular constituent in the collection by some biological mechanism, which need not be specified or even understood. In illustrations presented herein, the influence, whether direct or indirect, of one cellular constituent on another is presented as an arc between the two cellular constituents, and the entire pathway is presented as a network of arcs linking the cellular constituents of the pathway. A biological pathway, therefore, refers both to the collection of cellular constituents drawn from some aspect of the biological state together with the network of influences between the constituents.

For example, in FIG. 1, biological pathway 101 includes protein P1 (for example, either the abundance or activity of P1) and genes G1, G2, and G3 (for example, their transcribed mRNA levels) together with the influence, direct or indirect, of protein P1 on these three genes, represented as the arc leading from P1 to these three genes. The mechanism of this influence might arise, for example, because protein P1 can bind to promoters of these genes and increase the abundance of their transcripts.

Concrete examples of biological pathways, as understood herein, are well known in the art. They depend on various biological mechanisms by which the cellular constituents influence one another. Biological pathways include well-known biochemical synthetic pathways in which, for example, molecules are broken down to provide cellular energy or built up to provide cellular energy stores, or in which protein or nucleic acid precursors are synthesized. The cellular constituents of synthetic pathways include enzymes and the synthetic intermediates, and the influence of a precursor molecule on a successor molecule is by direct enzyme-mediated conversion. Biological pathways also include signaling and control pathways, many examples of which are also well known. Cellular constituents of these pathways include, typically, primary or intermediate signaling molecules, as well as the proteins participating in the signal or control cascades usually characterizing these pathways. In signaling pathways, binding of a signal molecule to a receptor usually directly influences the abundances of intermediate signaling molecules and indirectly influences on the degree of phosphorylation (or other modification) of pathway proteins. Both of these effects in turn influence activities of cellular proteins that are key effectors of the cellular processes initiated by the signal, for example, by affecting the transcriptional state of the cell. Control pathways, such as those controlling the timing and occurrence of the cell cycle, are similar. Here, multiple, often ongoing, cellular events are temporally coordinated, often with feedback control, to achieve a consistent outcome, such as cell division with chromosome segregation. This coordination is a consequence of functioning of the pathway, often mediated by mutual influences of proteins on each other's degree of phosphorylation (or other modification). Also, well known control pathways seek to maintain optimal levels of cellular metabolites in the face of a fluctuating environment. Further examples of cellular pathways operating according to understood mechanisms will be known to those of skill in the art.

Pathways of particular interest in this invention are defined as those that "originate" at particular cellular constituents. A pathway originating at particular cellular constituents includes those particular cellular constituents, a second group of cellular constituents that are directly influenced by the particular cellular constituents, a third group of cellular constituents that are directly influenced by the second group of cellular constituents, and so forth, along with the network of influences between the groups of cellular constituents. Influences between the cellular constituents can be according to any biological mechanism, for example, a signaling mechanism, or a regulatory or homeostatic control mechanism, or a synthetic mechanism. In FIG. 1, pathway 101, including a protein and several genes, originates at protein P1. Pathway 102, including two proteins and several genes, originates at proteins P2 and P3.

Biological pathways can also be either hierarchical or non-hierarchical. Generally, a hierarchical biological pathway has no feedback loops. In more detail, a hierarchical pathway is one in which its cellular constituents can be arranged into a hierarchy of numbered levels so that cellular constituents belonging to a particular numbered level can be influenced only by cellular constituents belonging to levels of lower numbers. A hierarchical pathway originates from the lowest numbered cellular constituents. In FIG. 1, pathways 101 and 102 are hierarchical. Pathway 101 is clearly hierarchical. In pathway 102, proteins P2 and P3, on a lowest numbered level, both (directly) affect gene G, on an intermediate numbered level. In turn, gene G (perhaps indirectly) affects genes G4, G5, and G6, all on a highest numbered level. In contrast, a non-hierarchical pathway has one or more feedback loops. A feedback loop in a biological pathway is a subset of cellular constituents of the pathway, each constituent of the feedback loop influences and also is influenced by other constituents of the feedback loop. For example, in pathway 102 of FIG. 1, if gene G6 (perhaps indirectly) affected protein P3, a feedback loop including genes G and G6 and protein P3 would be created.

In summary, therefore, as used herein, a biological pathway includes a collection of cellular constituents that influence one another through any biological mechanism, known or unknown, such as by a cell's synthetic, regulatory, homeostatic, or control networks. The influence of one cellular constituent on another can be, inter alia, by a synthetic transformation of the one cellular constituent into the other, by a direct physical interaction of the two cellular constituents, by an indirect interaction of the two cellular constituents mediated through intermediate biological events, or by other mechanisms. Further, certain pathways that are of particular interest in this invention can be said to originate at particular cellular constituents, which influence, but are not in turn influenced by, the other cellular constituents in the pathway and among such pathways, those without feedback loops are said to be hierarchical.

The present invention is directed to identifying multiple primary targets of drugs. Consequently, certain types of pathways are of particular interest. Drugs ideally act on a cell by directly interacting with one and only one cellular constituent. However, drugs typically act on a cell by directly interacting with multiple cellular constituents comprising 5 to 10 to 50 or more cellular constituents. Further effects of the drug on the cell flow from the other cellular constituents influenced, directly or indirectly, by the direct targets of the drug.

Figure 2:
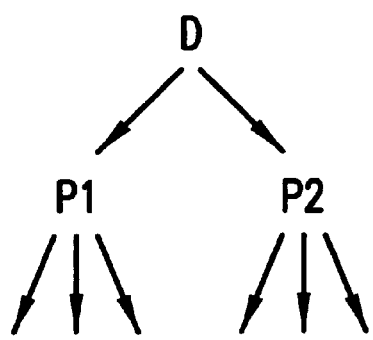
FIG. 2 illustrates exemplary biological pathways hypothesized for the action of a drug D on a biological system by acting on two primary targets: P1 and P2.

For example, FIG. 2 illustrates an exemplary biological pathway that includes a drug D acting on two primary targets: P1 and P2. Each primary target interacts, in turn, with a plurality of other cellular constituents, such as transcribed RNA levels, represented by the arcs leading from P1 and P2 (the individual cellular transcripts are not illustrated). Therefore, pathways of interest in this invention for identifying multiple primary targets of a drug include hierarchical pathways, such as the one shown in FIG. 2, which originate at a drug or compound of interest, or at the cellular constituents that are the primary targets of that drug. Since most drug targets are proteins, in particular, pathways originating at cellular proteins are of especial interest in representing drug action. Hierarchical pathways are advantageous in representing drug action, because the feedback loops present in non-hierarchical pathways can obscure drug effects by causing compensating influences in cellular constituents that mute drug influences.

5.2. Overview of the Methods of the Invention

The systems and methods of the present invention enable a user to identify the primary targets of a drug in a cell. In particular, the methods of the invention determine the number of primary targets of a drug by analyzing measurements of changes in the biological state of a cell in response to graded levels of drug exposure.

Aspects of the biological state of a cell, for example the transcriptional state, the translational state, or the activity state, are measured as described in Section 5.4 below, in response to a plurality of strengths of drug exposure. In embodiments wherein primary targets are to be identified for an environmental change, such measurements are made in response to a plurality of levels of the environmental change of interest, such as, for example, over a range of temperatures. Preferably, the strengths of drug exposure are graded from drug absence to full drug effect. The collection of these measurements, which may optionally be graphically represented, are called herein the "drug response" or "response profile." Each measured cellular constituent varying in the drug response is then analyzed to determine the particular drug concentration at which the cellular constituent is considered to have been activated or de-activated (for those cellular constituents which are inhibited in a drug response) according to some objective standard. The particular drug concentration that is so determined for a cellular constituent is called herein the "inflection point," or the "inflection concentration," or the "inflection drug concentration".

The inflection concentration for a cellular constituent is determined according to some objective standard. Typically, the drug response of a cellular constituent shows a behavior (for activation) where the slope first increase, reaches a maximum, and then decreases. In such instances, the inflection drug concentration is most preferably the drug concentration at which the drug response has a maximum slope. Likewise, in instances wherein a cellular constituent is inhibited by a drug, the drug response typically shows a behavior where the slope first decreases (i.e., becomes more negative), reaches a minimum (i.e., most negative) value, and the increases. In such instances, the inflection drug concentration is most preferably the drug concentration at which the drug response has a minimum slope. It will be recognized by those skilled in the art(s) that these two standards are essentially identical. In particular, in both instances the inflection concentration is the drug concentration wherein the absolute slope (i.e., the absolute value of the slope) of the drug response is maximum.

Alternatively, the inflection concentration may be determined to be the drug concentration at which the drug response of the cellular constituent is one-half of its asymptotic value. Other objective standards for determining the inflection concentration will be recognized by those skilled in the art(s). In fact, because the methods of the invention involve merely grouping cellular constituents with respect to the inflection concentration, the exact standard used is not crucial to enable one to practice the invention. It is important, however, that the inflection concentration be determined according to some objective standard, and that the same objective standard be used to determine the inflection drug concentration for all cellular constituents in a given drug response.

Because a given drug will most often have different potencies for different primary targets (i.e., each primary target tends to become inhibited at a different drug concentration) distinct sets of cellular constituents will be identified that have inflection points separated in drug concentration. Such sets of cellular constituents are referred to herein as "expression sets". Each expression set will thus contain cellular constituents which have similar inflection concentrations in the measured drug response.

The individual members (i.e., cellular constituents) of a given expression set correspond to cellular constituents which are downstream of a specific primary drug target in the drug response pathway. Thus, each expression cluster corresponds to a specific primary target of the drug, and so uniquely identifies that primary target.

5.3. Analytic Embodiments

The analytic embodiments of the methods of this invention include, first, embodiments for representing measured drug response data as a piecewise continuous drug response curve. The second aspect of the analytical embodiments of the invention comprises determining the "inflection point" or "inflection drug concentration" of the drug response curve. Finally, having determined the inflection drug concentration for a plurality of cellular constituents for which a drug response has been measured, the analytical embodiments of the invention involve a statistical analysis of the distribution of inflection drug concentrations. In particular, the "modality" of this distribution is determined, preferably according to an objective statistical method.

The analytical methods are described in detail in subsections 5.3.1 through 5.3.3 below. The present invention also provides systems which accept, e.g., as user input, drug response data and execute the analytical methods of the invention to determine multiple primary drug targets. Such systems are described below in subsection 5.3.4.

5.3.1. Drug Response Representation

The determination of multiple primary targets to a drug preferably begins by measuring drug response data. In many cases drug response data will have already been measured for graded levels of exposure to a particular drug or compound of interest. In other cases, this response data must be measured prior to the succeeding steps of the invention. As described above, these data are obtained by measuring changes in characteristics of cellular constituents at a plurality of levels of drug exposure (also called herein "levels of drug titration"). The drug exposure (or "drug titration") levels are preferably chosen so that five or more, more preferably ten or more, exposure values are present in the region where the characteristics of the cellular constituents rapidly change from native levels to saturation exposure levels.

In the following, the variable "t" is used to refer generally to drug exposure (or "titration") levels, and the variable "D" refers generally to the drug response data. In detail, the l'th measured drug exposure level is referred to as "$t_l$". The drug response for the k'th cellular constituent is "$D_k$". Therefore, $D_k(t_l)$ is the drug response of the k'th cellular constituent at the l'th level of drug exposure.

In the subsequent steps of these methods, values of the drug response data may be needed at values of the drug exposure which may not have been measured. In particular, in order to precisely define the inflection point of the drug response for any particular cellular constituent, it is preferable to provide drug response profile data which is smooth, or at least piece-wise continuous. It is therefore most preferable to provide for interpolating the drug response data to facilitate determination of the inflection drug concentration for each drug response $D_k$. This interpolation method is preferably accomplished either by spline fitting or by model-fitting.

In spline fitting, the drug response data are interpolated by summing products of an appropriate spline interpolation function, S, multiplied by the measured data values, as illustrated by the following equation.

$$D_k(x) = \sum_l S(x - t_l) D_k(t_l) \qquad (1)$$

The variable "x" refers to an arbitrary value of the drug exposure level at which the drug response data is to be evaluated. In general, S may be any smooth, or at least piece-wise continuous, function of limited support having a width characteristic of the structure expected in the response functions. An exemplary width can be chosen to be the distance over which the response function being interpolated rises from 10% to 90% of its asymptotic value. Different S functions may be appropriate for the drug and the pathway response data, and even for the response data of different pathways. Exemplary S functions include linear and Gaussian interpolation.

In model fitting, the drug responses are interpolated by approximating by a single parameterized function. An exemplary model-fitting function appropriate for approximating transcriptional state data is the Hill function, shown below in Equation 2.

$$H(x) = \frac{a(x/x_0)^n}{1 + (x/x_0)^n} \qquad (2)$$

The Hill function of Equation 2 comprises the adjustable parameters of: (1) an amplitude parameter a, and exponent m, and an inflection point parameter $x_0$. The adjustable parameters are selected independently for each cellular constituent of the drug response. Preferably, the adjustable parameters are selected so that for each cellular constituent of the drug response the sum of the squares of the distances of $H(t_l)$ from $D_k(t_l)$ is minimized. This preferable parameters adjustment method is known in the art as a least squares fit of $H()$ to $D_k()$. Such a fit may be done using any of the many available numerical methods (see, e.g., Press et al., 1996, *Numerical Recipes in C*, 2nd Ed., Cambridge Univ. Press, Chs. 10, 14; Branch et al., 1996, *Matlab Optimization Toolbox User's Guide, Mathworks*, Natick, Mass.).

Figure 4:
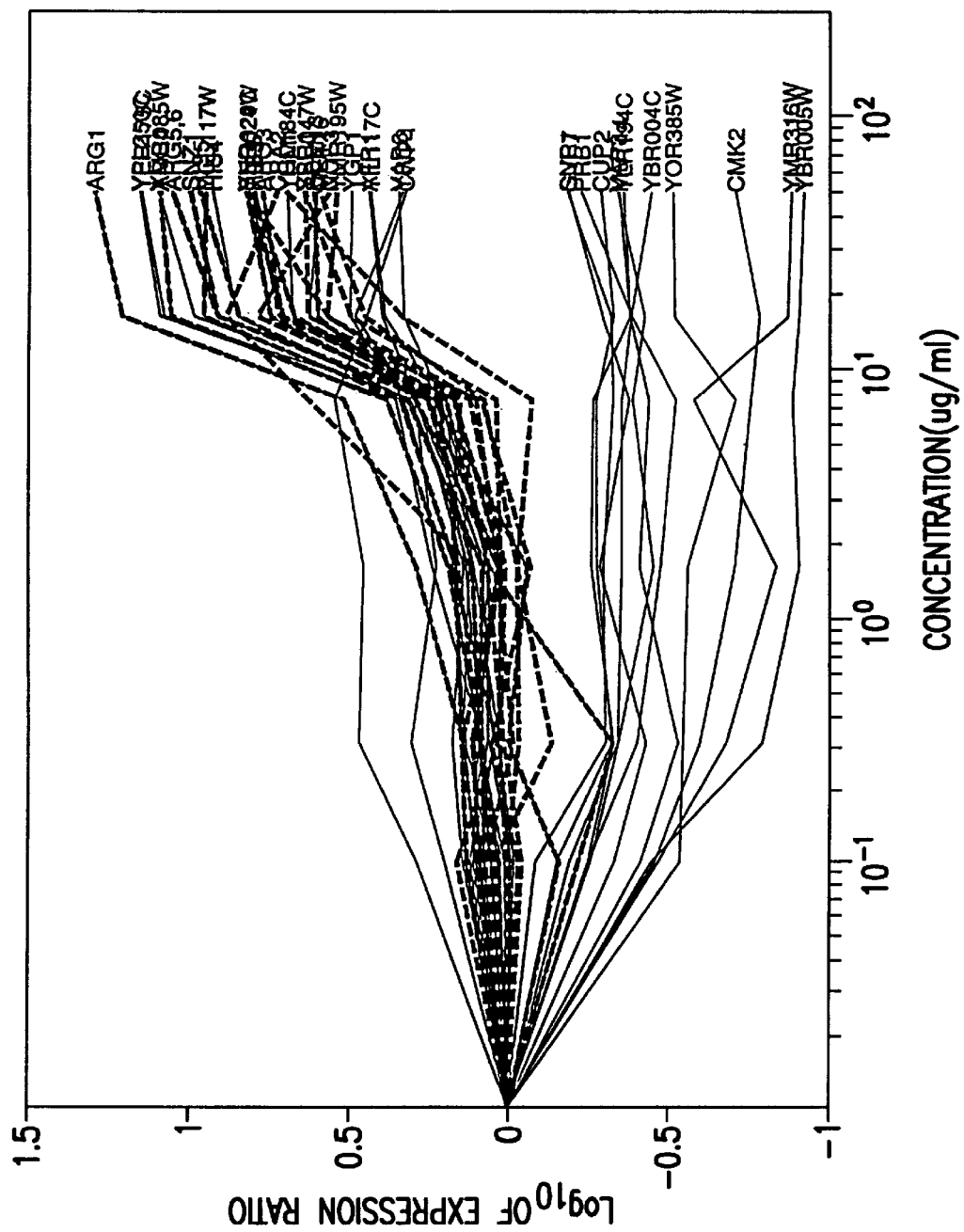
FIG. 4 illustrates drug response data of the 50 genes of *S. cerevisiae*, out of approximately 6000 measured genes, that had the largest expression ratio changes to the drug FK506; transcriptional effects shown in solid lines are via the calcineurin protein; transcriptional effects shown in dashed lines are via the Gcn4 transcription factor.
Figure 5:
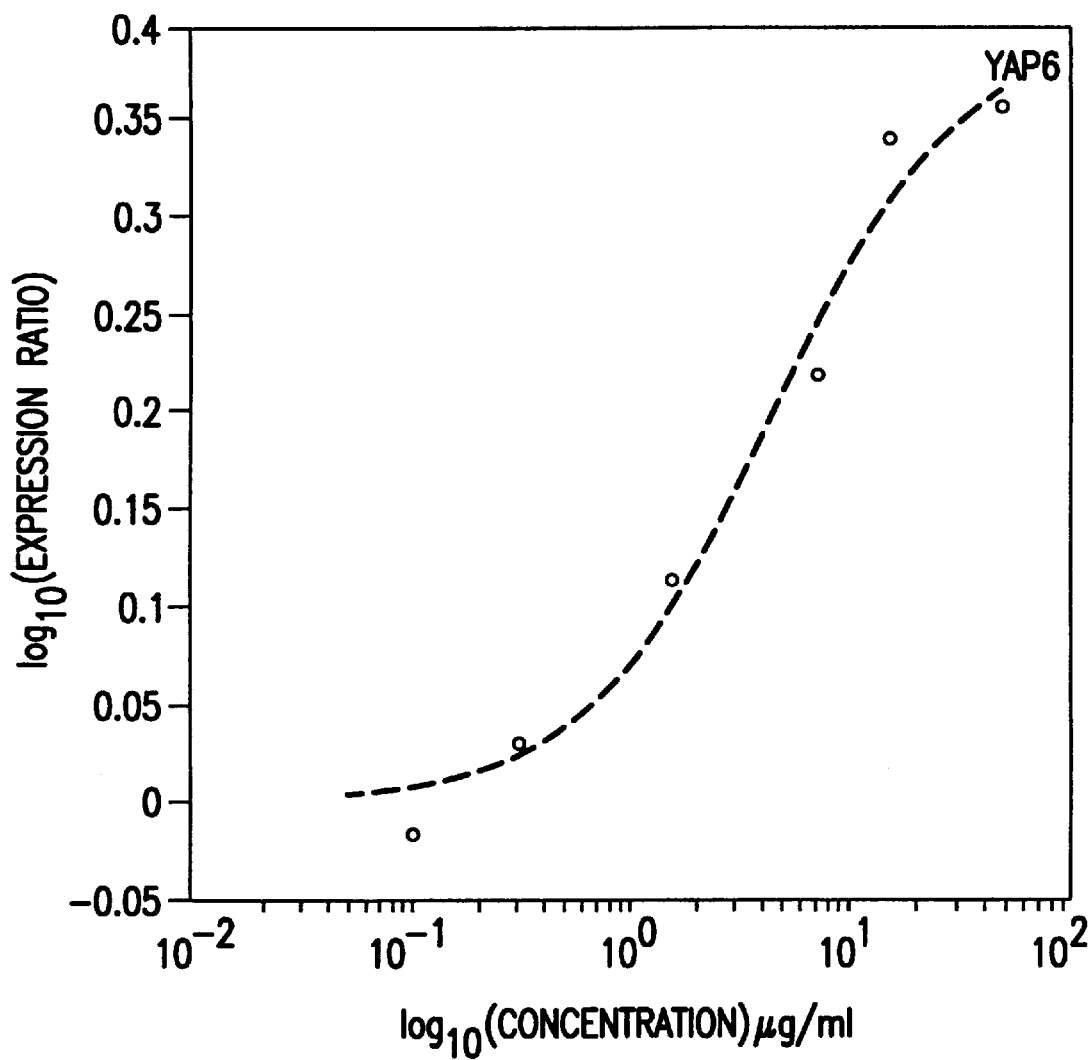
FIG. 5 illustrates the fit of a Hill function to the response of the *S. cerevisiae* gene YAP6 to FK506 illustrated in FIG. 4; the least squares fit to the Hill function (Equation 2) has an amplitude parameter a=0.4, a power exponent n=1, and $u_0=4.6$ (or $Log_{10}(u_0)=0.66$).

Model fitting with a Hill function is illustrated with respect to FIGS. 4 and 5. FIG. 4 illustrates an example of titration with the drug FK506. This figure illustrates the RNA expression levels of 50 genes of the yeast *S. cerevisiae* that, of the approximately 6000 genes in the genome of this organism, had the largest expression changes in response to graded levels of exposure to FK506. FIG. 5 illustrates a fit of the drug response of one of these gene expression levels by a Hill function. In particular, the yeast gene YAP6 was fit by a Hill function with parameters a=0.4, n=1, and $Log_{10}(u_0)$=0.66 (or $u_0$=4.6) selected by the previously described least squares method.

Since all of the 50 genes with the largest response to FK506 behaved monotonically, i.e., none of the responses decreased significantly from its maximum amplitude (or increased significantly from its minimum amplitude) with increasing drug exposure, the Hill function is an appropriate model fitting function. For non-monotonic behavior the Hill function would not be an appropriate model fitting function. Other possible model functions are based on polynomial fitting, for example by various known classes of polynomials.

5.3.2. Inflection Drug Concentration

After selection of a response data interpolation method, the next step of identifying primary drug targets is the determination of the inflection point (i.e., of the inflection drug concentration) for each cellular constituent's drug response. In general, the inflection drug concentration will be determined from the absolute maximum derivative of the interpolated drug response, i.e., from the expression $$\max_{(x)} \left| \frac{d D_k(x)}{d x} \right| \quad (3)$$

In other, alternative embodiments the inflection concentration can be defined as the drug concentration at which the drug response (e.g., transcription level) has one-half its asymptotic value. This method is particularly preferred in embodiments wherein the response data is fit to a Hill function as described above. In such embodiments, the inflection drug concentration is simply the value of the inflection point parameter $x_0$ in the least squares fit of the response data. Other definitions and methods for determining the inflection concentration will be apparent to those skilled in the art. Such definitions and methods are intended to be within the scope of the present invention.

5.3.3. Statistiscal Analysis

According to the present invention, individual primary targets of a drug engage multiple secondary and tertiary gene expression changes that form coherent expression sets that "turn on" at specific concentrations of a drug. Thus, multiple primary targets of a drug are simultaneously identified in the invention by identifying coherent sets of cellular constituents which "turn on", i.e., have inflection points, at a specific drug concentration. Such "expression sets" of cellular constituents may be readily identified from a histogram of the determined inflection drug concentration values, $x_0$. For example, FIG. 6 shows the histogram of inflection drug concentration values, $x_0$ for the 50 largest gene responses when titrating S. cerevisiae with the drug FK506. In many embodiments, expression sets of cellular constituents may be readily identified by visual inspection of the histogram. For example, the inflection concentrations of the histogram shown in FIG. 6 clearly cluster around two different drug concentrations: ~0.3 µg/ml and ~20 µg/ml.

It will be recognized by one skilled in the art that a histogram, such as the one shown in FIG. 6, indicates a distribution of some quantity. In particular, a histogram such as the one shown in FIG. 6 represents a statistical distribution of some quantity, e.g., inflection drug concentrations of the plurality of cellular constituents. Accordingly, it will be readily apparent to one skilled in the art that, for purposes of describing and claiming the present invention, the terms "distribution," "statistical distribution," and "histogram" may be used interchangeably.

A statistical distribution such as the one shown in FIG. 6 is known in the art as a "bimodal" distribution. In other words, the distribution of inflection drug concentrations in FIG. 6 has two distinct "modes": one of ~0.3 µg/ml and another of ~20 µg/ml. Thus, each expression set corresponds to a particular mode in the distribution (i.e., in the histogram) of the inflection drug concentrations determined from the drug response. Other distributions are possible, and even expected, for different drugs. For example, a distribution may be "unimodal," "trimodal," etc. (i.e., may have one, three, etc. modes of distribution). More generally, a statistical distribution that has more than one mode of distribution is said to be "multimodal."

In other embodiments, the multimodality of a statistical distribution, in particular a distribution of inflection concentrations, is not immediately obvious by mere visual inspection of the histogram. In such instances, the modality of the distribution may be determined using objective statistical tests which are well known in the art (see, e.g., Phillips, T. Y. et al., 1989, *Pattern Recognition* 22:741–746). Preferably, the objective statistical test for determining multimodality is model independent, and therefore robust to uncertainty as to the shape of the component distributions which may occur at preferred values of $x_0$. For example, in one particular embodiment, the statistical test for bimodality is based on the Fisher Distance.

In determining the Fisher Distance of a distribution, the distribution itself is first divided at some arbitrary value, specified by a binning parameter γ. The divided distribution then consists of a "left part" having $n_1$ elements and a "right part" having $n_2$ elements, wherein $N = n_1 + n_2$ is the number of elements in the entire distribution. In particular, in the present invention n is the number of cellular constituents included in the distribution.

Each part of the thus divided distribution (i.e., the left and right parts) will have its own mean ($\mu_1$ and $\mu_2$) and second moment ($\sigma_1$ and $\sigma_2$), which are determined by expressions well known to those skilled in the art. The Fisher Distance FD is determined from the mean and second moment of the left and right parts of the divided distribution according to Equation 4.

$$FD^2(\gamma) = \frac{N[\mu_1(\gamma) - \mu_2(\gamma)]^2}{n_1 \sigma_1^2(\gamma) + n_2 \sigma_2^2(\gamma)} \quad (4)$$

In order to evaluate the "confidence level" for declaring a distribution bimodal, the Fisher Distance FD is preferably optimized or maximized by selecting the binning parameter γ such that $$FD_{\max} = \max_{(\gamma)} FD(\gamma) \quad (5)$$

A higher value of $FD_{max}$ indicates a greater level of confidence that a specific distribution is indeed bimodal. In another embodiment, the confidence level of declaring a distribution bimodal is determined quantitatively by comparing the actual value of $FD_{max}$, determined for a particular distribution of inflection concentrations, to an empirically determined (e.g., by Monte Carlo realizations of the actual data) distribution of $FD_{max}$ values generated under the null hypothesis of unimodality. Histogram realizations drawn from most unimodal histogram population distribution shapes are found to give very similar distributions of $FD_{max}$. Thus, in various alternative embodiments, the unimodal distribution may have a variety of shapes. For example, in alternative embodiments, the unimodal distribution shape may be, e.g., uniform, triangular, or Guassian. Preferably, the empirically determined $FD_{max}$ values are determined with the same number of elements and same binning resolution as the actual response data. However, Monte Carlo results for unimodal distributions have also been found to be insensitive to both the number of elements, and to the binning resolution. Thus, in other embodiments the empirical $FD_{max}$ distribution may be determined with a different number of elements and/or different binning resolution than the actual response data.

From such unimodal results, it is possible to assign a probability value that an actual $FD_{max}$ value determined for a distribution of inflection concentrations actually comes from a unimodal distribution. Specifically this probability, P, is simply the fraction of $FD_{max}$ values in an empirical unimodal distribution of $FD_{max}$ which are greater than the determined $FD_{max}$. Such a fraction will correspond, as will be recognized by one skilled in the art, to the area of the histogram of the empirical unimodal distribution of $FD_{max}$ values to the right of the actual, determined $FD_{max}$ value. Thus, the confidence level for declaring bimodality is the probability that the determined $FD_{max}$ is from a unimodal distribution subtracted from unity, i.e., 1–P.

In other embodiments, it is desirable to test for higher levels of modality in the distribution of inflection drug concentrations. In such embodiments, multimodality can be assessed by dividing the histogram interval into subintervals which are suspected of containing two distinct modes, and employing the above described test for bimodality to each subinterval.

5.3.4. Implementation Systems and Methods

Figure 3:
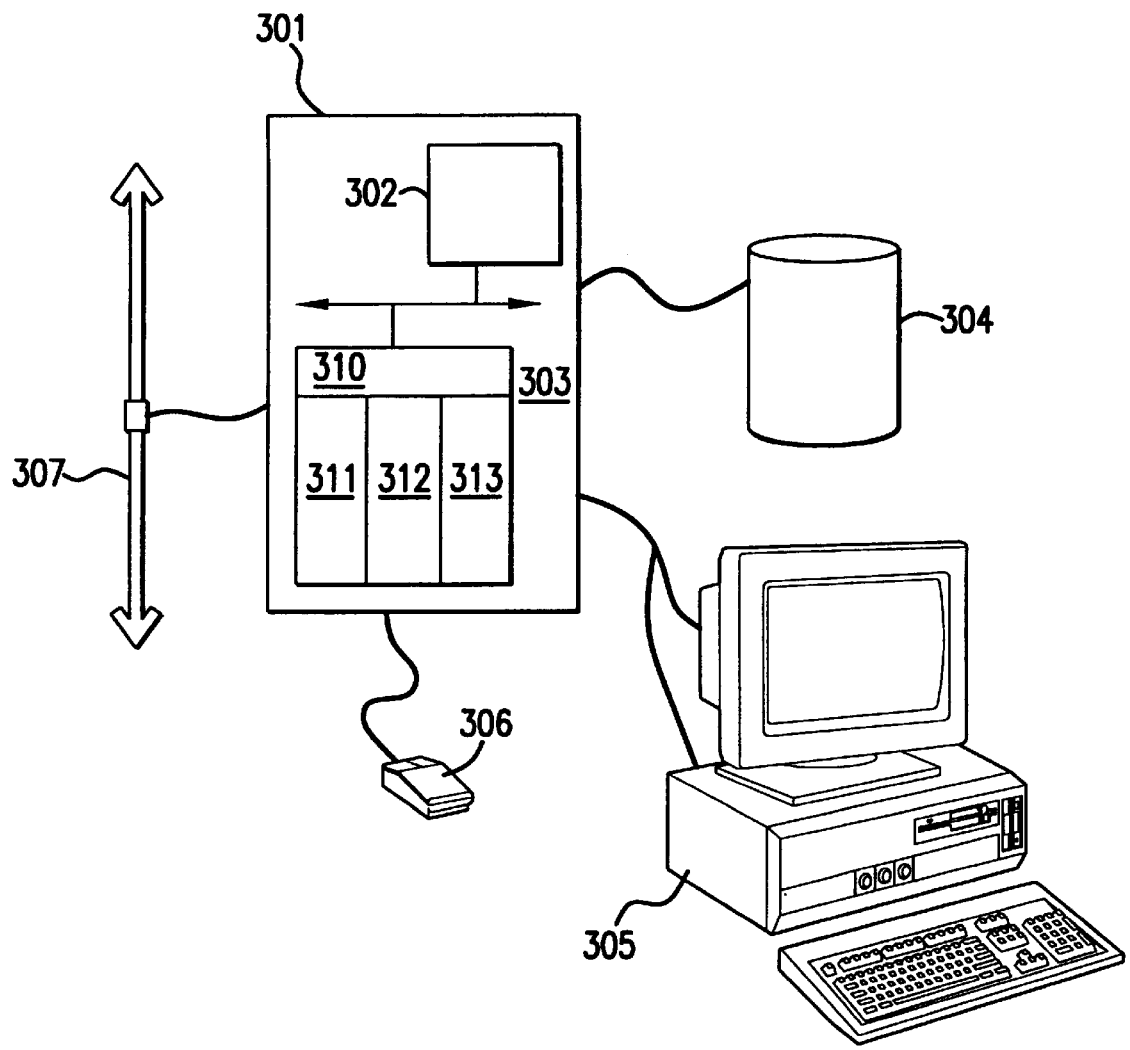
FIG. 3 illustrates an exemplary embodiment of a computer system of the present invention.

The analytic methods described in the previous subsections are preferably implemented by use of a computer system. Accordingly, the present invention also provides a computer system for practicing the methods of the invention according to the following programs and methods. FIG. 3 illustrates an exemplary computer system suitable for implementation of the analytic methods of this invention. Computer system 301 is illustrated as comprising internal components and being linked to external components. The internal components of this computer system include processor element 302 interconnected with main memory 303. For example, computer system 301 can be a Intel Pentium®-based processor of 200 MHz or greater clock rate and with 32 MB or more of main memory.

The external components include mass storage 304. This mass storage can be one or more hard disks (which are typically packaged together with the processor and memory). Such hard disks are typically of 1 GB or greater storage capacity. Other external components include user interface device 305, which can be a monitor and keyboard, together with pointing device 306, which can be a "mouse", or other graphic input devices (not illustrated). Typically, computer system 301 is also linked to network line 307, which can be part of an Ethernet link to other local computer systems, remote computer systems, or wide area communication networks, such as the Internet. This network link allows computer system 301 to share data and processing tasks with other computer systems. The components of the computer system may also include means for displaying data, such as means for displaying the drug response data, inflection drug concentrations, and/or expression sets. Such means may include, but are by no means limited to, a monitor, or a printer or plotter.

Loaded into memory during operation of this system are several software components, which are both standard in the art and special to the instant invention. These software components collectively cause the computer system to function according to the methods of this invention. These software components are typically stored on mass storage 304. Software component 310 represents the operating system, which is responsible for managing computer system 301 and its network interconnections. This operating system can be, e.g., of the Microsoft Windows™ family, such as Windows 95, Windows 98, or Windows NT, a Macintosh operating system, and OS/2 operating system, or a Unix operating system. Software component 311 represents common languages and functions conveniently presented on this system to assist programs implementing the methods specific to this invention. Languages that can be used to program the analytic methods of this invention include C, and C++, and, less preferably, JAVA®. Most preferably, the methods of this invention are programmed in mathematical software packages which allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), or S-Plus from Math Soft (Seattle, Wash.).

Software components 312 and 313 and 314 represent the analytic methods of this invention as programmed in a procedural language or symbolic package. Component 312 represents programs or subroutines implementing the methods for drug response representation described in Section 5.3.1, above. Component 313 represents programs or subroutines implementing the methods for determining the inflection drug concentration for each drug response (i.e., for the drug response of each cellular constituent), and component 314 represents programs of subroutines implementing the methods for determining the distribution of inflection drug concentrations including the objective statistical test for bimodality or multimodality described in Section 5.3.3.

In an exemplary implementation, to practice the methods of the invention using such a computer system, a user loads drug response data into computer memory 303. These data can be directly entered by the user from monitor and keyboard 305, or from other computer systems linked by network connection 307, or on removable storage media (not illustrated). Next, the user causes execution of drug response representation software 312, followed by execution of software component 313, which determines inflection concentrations from one or more drug responses according to the methods of Section 5.3.2 above, and software component 314 which determines statistical distribution of the determined inflection concentrations according to the methods of Section 5.3.3 above.

In an alternative implementation, to practice the methods of the invention using such a computer system, a user loads into computer memory 303 inflection concentration values for a plurality of cellular constituents determined from drug response data. These data can be entered according to any of the methods described above for entering drug response data. In such an embodiment, software components 312 and 313 are not used, and need not be included in the computer system. Rather, software component 314 is executed to determine the distribution and modality of the loaded inflection concentration values.

Alternative systems and methods for implementing the analytic methods of this invention will be apparent to one of skill in the art, and are intended to be comprehended within the accompanying claims. In particular, the accompanying claims are intended to include alternative program structures for implementing the methods of this invention that will be readily apparent to one of skill in the art.

5.4. Measurement Methods

Drug responses are obtained for use in the instant invention by measuring the cellular constituents changed by drug exposure or by pathway perturbation. These cellular characteristics can be of any aspect of the biological state of a cell. They can be, e.g., of the transcription state, in which RNA abundances are measured, the translation state, in which protein abundances are measured, the activity state, in which protein activities are measured. The cellular characteristics can also be of mixed aspects, for example, in which the activities of one or more proteins originating a particular biological pathway are measured along with RNA abundances (gene expression) of cellular constituents in the pathway downstream of the originating protein(s). This section describes exemplary methods for measuring the cellular constituents in drug or pathway responses. This invention is adaptable to other methods of such measurement.

Embodiments of this invention based on measuring the transcriptional state of drug and pathway responses are preferred. The transcriptional state can be measured by techniques of hybridization to arrays of nucleic acid or nucleic acid mimic probes, described in the next subsection, or by other gene expression technologies, described in the subsequent subsection. However, measured, the result is response data including values representing RNA abundance ratios, which usually reflect DNA expression ratios (in the absence of differences in RNA degradation rates). Such measurement methods are described in Section 5.4.1.

In various alternative embodiments of the present invention, aspects of the biological state other than the transcriptional state, such as the translational state, the activity state, or mixed aspects can be measured. Details of these embodiments are described in this section. Such measurement methods are described in Section 5.4.2.

5.4.1. Measurement of Drug Response Data

To measure drug response data, cell are exposed to graded levels of the drug or drug candidate of interest. When the cells are grown in vitro, the compound is usually added to their nutrient medium. In the case of yeast, such as S. cerevisiae, it is preferably to harvest the cells in early log phase, since expression patterns are relatively insensitive to time of harvest at that time. The drug is added in a graded amount that depends on the particular characteristics of the drug, but usually will be between about 1 ng/ml and 100 mg/ml. In some cases a drug will be solubilized in a solvent such as DMSO.

The biological state of cells exposed to the drug and cells not exposed to the drug is measured according to any of the below described methods. Preferably, transcript or microarrays are used to find the mRNAs with altered expression due to exposure to the drug. However, other aspects of the biological state may also be measured to determine, e.g., proteins with altered translation or activities due to exposure to the drug.

It is preferable for measurements of drug responses, in the case of two-colored differential hybridization described below, to measure also with reversed labeling. Also, it is preferable that the levels of drug exposure used provide sufficient resolution of rapidly changing regions of the drug response, e.g., by using approximately ten levels of drug exposure.

5.4.2. Transcriptional State Measurement

In general, measurement of the transcriptional state can be performed using any probe or probes which comprise a polynucleotide sequence and which are immobilized to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probe may be full or partial sequences of genomic DNA, cDNA, or mRNA sequences extracted from cells. The polynucleotide sequences of the probes may also be synthesized nucleotide sequences, such as synthetic oligonucleotide sequences. The probe sequences can be synthesized either enzymatically in vivo, enzymatically in vitro, (e.g., by PCR), or non-enzymatically in vitro.

The probe or probes used in the methods of the invention are preferably immobilized to a solid support or surface which may be either porous or non-porous. For example, the probes of the invention may be polynucleotide sequences which are attached to a nitrocellulose or nylon membrane or filter. Such hybridization probes are well known in the art (see, e.g., Sambrook et al., Eds., 1989, *Molecular Cloning: A Laboratory Manual,* 2nd ed., Vols. 1–3, Cold Spring Harbor Laboratory, Cold Spring Harbor, N.Y.). Alternatively, the solid support or surface may be a glass or plastic surface.

5.4.2.1. Microarrays Generally

In a particularly preferred embodiment, measurement of the transcriptional state are made by hybridization to microarrays of probes consisting of a solid phase, on the surface of which are immobilized a population of polynucleotides, such as a population of DNA or DNA mimics, or, alternatively, a population of RNA. Specifically, a microarray is an array of less than 6.25 $cm^2$ in size. Microarrays can be employed, e.g., for analyzing the transcriptional state of a cell, such as the transcriptional states of cells exposed to graded levels of a drug of interest.

In preferred embodiments, a microarray comprises a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably, the microarrays are small, usually smaller than 5 $cm_2$, and they are made from materials that are stable under binding (e.g., nucleic acid hybridization) conditions. Preferably, a given binding site or unique set of binding sites in the microarray will specifically bind (e.g., hybridize) to the product of a single gene in a cell (e.g., to a specific mRNA, or to a specific cDNA derived therefrom). However, as discussed supra, in general other, related or similar sequences will cross hybridize to a given binding site. Although there may be more than one physical binding site per specific RNA or DNA, for the sake of clarity the discussion below will assume that there is a single, completely complementary binding site.

The microarrays of the present invention include one or more test probes, each of which has a polynucleotide sequence that is complementary to a subsequence of RNA or DNA to be detected. Each probe preferably has a different nucleic acid sequence. The position of each probe on the solid surface is preferably known. In one embodiment, the microarray is a high density array, preferably having a density greater than about 60 different probes per 1 cm$^2$. In one embodiment, the microarray is an array (i.e., a matrix) in which each position represents a discrete binding site for a product encoded by a gene (i.e., an mRNA or a cDNA derived therefrom), and in which binding sites are present for products of most or almost all of the genes in the organism's genome. For example, the binding site can be a DNA or DNA analogue to which a particular RNA can specifically hybridize. The DNA or DNA analogue can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often to about 75%, more often to at least about 85%, even more often to about 90%, and still more often to at least about 99%. Preferably, the microarray has binding sites for genes relevant to the action of a drug of interest or in a biological pathway of interest. A "gene" is identified as an open reading frame ("ORF") which encodes a sequence of preferably at least 50, 75, or 99 amino acids from which a messenger RNA is transcribed in the organism or in some cell in a multicellular organism. The number of genes in a genome can be estimated from the number of mRNAs expressed by the organism, or by extrapolation from a well characterized portion of the genome. When the genome of the organism of interest has been sequenced, the number of ORF's can be determined and mRNA coding regions identified by analysis of the DNA sequence. For example, the genome of *Saccharomyces cerevisiae* has been completely sequenced, and is reported to have approximately 6275 ORFs longer than 99 amino acids. Analysis of the ORFs indicates that there are 5885 ORFs that are likely to encode protein products (Goffeau et al., 1996, *Science* 274:546–567). In contrast, the human genome is estimated to contain approximately 10$^5$ genes.

5.4.2.2. Preparing Probes for Microarrays

As noted above, the "probe" to which a particular polynucleotide molecule specifically hybridizes according to the invention is usually a complementary polynucleotide sequence. In one embodiment, the probes of the microarray are DNA or DNA "mimics" (e.g., derivatives and analogues) corresponding to at least a portion of each gene in an organism's genome. In another embodiment, the probes of the microarray are complementary RNA or RNA mimics.

DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtain, e.g., by polymerase chain reaction ("PCR") amplicafication of gene segments from genomic DNA, cDNA (e.g., by RT-PCR), or clones sequences. PCR primers are preferably chosen based on known sequences of the genes or cDNA that result in amplification of unique fragments (i.e.g, fragments that do not share more than 10 bases of contiguous identical sequence with any other fragment on the microarray). Computer programs that are well known in the art are useful in the design of primer with the required specificity and optimal amplification properties, such as Oligo version 5.0 (National Biosciences). Typically, each probe of the microarray will be between about 20 bases and about 12,000 bases, and usually between about 300 bases and about 2,000 bases in length, and still more usually between about 300 bases and about 800 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399–5407; McBrid et al., 1983, *Tetrahedron Lett.* 24:246–248). Synthetic sequences are typically between about 15 and about 500 bases in length, more typically between about 20 and about 50 bases. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566–568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207–209).

5.4.2.3. Attaching Probes to the Solid Surface

The probes are attached to a solid support or surface, which may be made, e.g., from glass, plastic (e.g., polypropylene, nylon), polyacrylamide, nitrocellulose, or other materials. A preferred method for attaching the nucleic acids to a surface is by printing on glass plates, as is described generally by Schena et al., 1995, *Science* 270:467–470. This method is especially useful for preparing microarrays of cDNA (See also, DeRisi et al., 1996, *Nature Genetics* 14:457–460; Shalon et al., 1996, *Genome Res.* 6:689–645; and Schena et al., 1995, *Proc. Natl. Acad. Sci. U.S.A.* 93:10539–11286). Blanchard discloses the use of an ink jet printer for oligonucleotide synthesis (U.S. application Ser. No. 09/008,120, filed Jan. 16, 1998).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767–773; Pease et al., 1994, *Proc. Natl. Acad. Sci. U.S.A.* 91:5022–5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687–690). When these methods are used, oligonucleotides (e.g., 20-mers) of known sequence are synthesized directly on a surface such as a derivatized glass slides. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids. Res.*

20:1679–1684), may also be used. In principle, any type of array, for example, dot blots on a nylon hybridization membrane (see Sambrook et al., supra) could be used. However, as will be recognized by those skilled in the art, very small arrays will frequently be preferred because hybridization volumes will be smaller.

5.4.2.4. Target Polynucleotide Molecules

As described, supra, the polynucleotide molecules which may be analyzed by the present invention may be from any source, including naturally occurring nucleic acid molecules, as well as synthetic nucleic acid molecules. In a preferred embodiment, the polynucleotide molecules analyzed by the invention comprise RNA, including, but by no means limited to, total cellular RNA, poly(A)$^+$ messenger RNA (mRNA), fractions thereof, or RNA transcribed from cDNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). Poly (A)+ RNA is selected by selection with oligo-dT cellulose. Cells of interest include, but are by no means limited to, wild-type cells, drug-exposed wild-type cells, modified cells, diseased cells, and, in particular, cancer cells.

In one embodiment, RNA can be fragmented by methods known in the art, e.g., by incubation with $ZnCl_2$, to generate fragments of RNA. In one embodiment, isolated mRNA can be converted to antisense RNA synthesized by in vitro transcription of double-stranded cDNA in the presence of labeled dNTPs (Lockhart et al., 1996, *Nature Biotechnology* 14:1675).

In other embodiments, the polynucleotide molecules to be analyzed may be DNA molecules such as fragmented genomic DNA, first strand cDNA which is reverse transcribed from mRNA, or PCR products of amplified mRNA or cDNA.

5.4.2.5. Hybridization to Microarrays

Nucleic acid hybridization and wash conditions are chosen so that the polynucleotide molecules to be analyzed by the invention "specifically bind" or "specifically hybridize" to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA or DNA) of probe and target nucleic acids. General parameters for specific (i.e., stringent) hybridization conditions are described in Sambrook et al. (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5× SSC plus 0.2% SDS at 65° C. for four hours, followed by washes at 25° C. in high stringency wash buffer (0.1× SSC plus 0.2% SDS) (Shena et al., 1996, *Proc. Natl. Acad. Sci. U.S.A.* 93:10614). Useful hybridization conditions are also provided, e.g., Tijessen, 1993, *Hybridization With Nucleic Acid Probes*, Elsevier Science Publishers B.V.; and Kricka, 1992, *Nonisotopic DNA Probe Techniques*, Academic Press, San Diego, Calif.

5.4.2.6. Signal Detection and Data Analysis

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses, one cell is exposed to a drug and another cell of the same type is not exposed to the drug. The cDNA derived from each of the two cell types are differently labeled so that they can be distinguished. In one embodiment, for example, cDNA from a cell treated with a drug is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA is thereby detected.

In the example described above, the cDNA from the drug-treated cell will fluoresce green when the fluorophore is stimulated, and the cDNA from the untreated cell will fluoresce red. As a result, when the drug treatment has no effect, either directly or indirectly, on the relative abundance of a particular mRNA in a cell, the mRNA will be equally prevalent in both cells, and, upon reverse transcription, red-labeled and green-labeled cDNA will be equally prevalent. When hybridized to the microarray, the binding site(s) for that species of RNA will emit wavelength characteristic of both fluorophores. In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, *Science* 270:467–470. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

When fluorescently labeled probes are used, the fluorescence emissions at each site of a transcript array can be, preferably, detected by scanning confocal laser microscopy.

In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639–645). In a preferred embodiment, the arrays are scanned with a laser fluorescent scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639–645. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as a perturbation and its magnitude determined (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

5.4.2.7. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent 0 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci. U.S.A.* 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, *Science* 270:484–487).

Such methods and systems of measuring transcriptional state, although less preferable than microarrays, may, nevertheless, be used in the present invention.

5.4.3. Measurements of Other Aspects of Biological State

Although monitoring cellular constituents other than mRNA abundances currently presents certain technical difficulties not encountered in monitoring mRNAs (i.e., the transcriptional state), it will be apparent to those skilled in the art that the use of methods of this invention are applicable to any cellular constituent that can be monitored.

In various embodiments of the present invention, aspects of the biological state other than the transcriptional state, such as the translational state, the activity state, or mixed aspects thereof can be measured in order to obtain drug responses for the present invention. Details of these embodiments are described in this section.

5.4.3.1. Translational State Measurements

Measurements of the translational state may be performed according to several methods. For example, whole genome monitoring of protein (i.e., the "proteome," Goffea et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y.). In a preferred embodiment, monoclonal antibodies are raised against synthetic peptide fragments designed based on genomic sequence of the cell. With such an antibody array, proteins from the cell are contacted to the array, and their binding is assayed with assays known in the art.

Alternatively, proteins can be separated by two-dimensional gel electrophoresis systems. Two-dimensional gel electrophoresis is well known in the art, and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Scie. U.S.A.* 93:1440–1445; Sagliocco et al., 1996, *Yeast* 12:1519–1533; and Lander, 1996, *Science* 274:536–539. The resulting electropherograms can be analyzed by numerous techniques, including mass spectrometric techniques, western blotting, and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

5.4.3.2. Activity State Measurements

Where activities of proteins relevant to the characterization of drug action can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known or measured, the changes in protein activities form the response data analyzed by the foregoing methods of this invention.

5.4.3.3. Mixed Aspects of Biological State

In alternative and non-limiting embodiments, response data may be formed of mixed aspects of the biological state of a cell. Response data can be constructed from combinations of, e.g., changes in certain mRNA abundances, changes in certain protein abundances, and changes in certain protein activities.

6. EXAMPLES

The following examples of determining multiple drug targets are presented by way of illustration of the previously described invention and are not limiting of that description.

6.1. Identification of Dual Primary Targets

This example illustrates the application of the methods of the present invention to identify two distinct primary targets of a particular drug: FK506. In particular, FK506 is known to act via two separate protein pathways in *S. cerevisiae*; the first via the calcineurin protein, and the second via the Gcn4 transcription factor. Thus, FK506 has two primary targets in yeast.

Cultured *S. cerevisiae* were titrated with graduates levels of FK506 and transcription levels were measured according to the methods described above in Section 5.4. Drug responses for the 50 genes which had the largest expression changes in response to FK506 are plotted in FIG. 4. The vertical axis is the $\text{Log}_{10}$ of the expression ratio, i.e., the ratio between the mRNA level measured with drug treatment and the mRNA level measured with drug absent. Two groups of transcriptional response can be distinguished in the plot. One group saturates at approximately 0.3 μg/ml of FK506, whereas the second group turns on later at a dose of approximately 20 μg/ml.

Each of the fifty drug responses shown in FIG. 4 was fit to a Hill function (Equation 2 above) and their inflection drug concentration was determined from the fit parameter $x_0$. FIG. 6 shows the histogram of inflection drug concentrations. The bimodal distribution of the inflection concentrations is readily apparent through simple visual inspection of the histogram. In particular, the inflection drug concentrations cluster around two distinct values; one near 0.3 μg/ml, and another near 20 μg/ml.

These clusters correspond to specific "sets" of cellular constituents which are affected by different primary targets of FK506. Specifically, those cellular constituents which are activated (or deactivated) at a lower drug concentration (i.e., that have an inflection concentration near 0.3 μg/ml) are activated (or deactivated) via the calcineurin protein, whereas those cellular constituents which are activated (or deactivated) at a higher drug concentration (i.e., that have an inflection concentration near 20 μg/ml) are activated via the Gcn4 transcription factor. Thus, each "set" or mode shown in FIG. 6 identifies a specific primary target of the drug FK506.

6.2. Identification of a Single Primary Target

This example illustrates, in contrast to the Example presented in Section 6.1 above, the application of the methods of the present invention to identify the action of a drug via a single primary target. In particular, two yeast strains were constructed containing genes under the control of a Tet promoter system (see Brachmann, C. B., et al., 1998, *Yeast* 14:115–132; Gari, E., et al., 1997, *Yeast* 13:837–848; Jones, J. S., and Prakash, L., 1990, *Yeast* 6:363–366; and Wach, A. A.; et al., 1994, *Yeast* 10:1793–1808). The first yeast strain, R1918, contained HMG2 under control of the Tet promoter. The second yeast strain, R1446, contained ERG11 regulated by a Tet promoter system.

Construction of Yeast Strain R1918

Plasmids for the yeast strain R1918 were constructed as follows. For gene disruption in yeast, the kanR dominant selectable marker (see Wach et al., supra) was amplified from pUCkanR, which consists of a 1.5 kb EcoRI-BamHI kanR fragment from pFA-kanMX6 cloned into the EcoRI-BamHI sites of pUC18. The kamR-tetO7 promoter replacement vector pkantetO7 was constructed by modifying pUC-kanR with a linker that introduced XhoI and BamHI sites adjacent to the kanR gene, resulting in pUCkanXB. A 700 bp XhoI-BamHI fragment from pCM159 (see, Gari et al, supra), containing the ADH1 terminator, the tetO7 operator, and the TATA element from CYC1 was cloned into the XhoI-BamHI sites of pUCkanXB, creating pkantetO7. The vector pURA3tTA* consists of a 1.9 kb XhoI-EcoRI fragment, containing the CMV (cytomegalovirus) promoter and the tTA* transcriptional activator (Gari et al., supra) cloned into the SalI-EcoRI of pJJ242, which contains the URA3 gene cloned in pUC18 (Jones and Prakash, supra).

Yeast strain R1918 was constructed as follows. The hmg1:kanR/HMG1 heterozygous diploid strain R535 was constructed by transforming the diploid strain By4743 (Brachmann et al., supra) with a PCR-amplified kanR fragment flanked on both sides with 55 bp of homology to HMG1 such that, upon recombining at the HMG1 locus, the entire coding region, including the start and stop codons, were replaced with the kanR gene. R535 was sporulated, and tetrad dissection led to the isolation of the MATα hmg1::kanR haploid strain R1012.

The MATa haploid strain R1200, which expresses the tTA* transcriptional activator, was constructed by targeting the 3.2 kb URA3-CMVp-tTA* construct (PCR amplified from pURA3tTA*) to the ura3-0 locus of haploid strain BY4741 (Brachmann et al., supra) by PCR-mediated gene replacement. To replace the endogenous HMG2 promoter with the tetO7 promoter, R1200 was transformed with a PCR-amplified 2.2 kb kanR-tetO7 fragment flanked by HMG2 homology. Homologous integration of this fragment at the HMG2 promoter region resulted in replacement of the 352 bp immediately upstream of the ATG with kanR-tetO7. This resulted in strain R1159 (MATa, URA3-CMVp-tTA*, tetO7-HMG2).

R1159 and R1012 were crossed to create the diploid strain R1525 with genotype MATa/α; hmg1::kanR/HMG1; kanR-tetO7-HMG2/HMG2; URA3-CMVp-tTA*/ura3-0. Sporulation and tetrad dissection led to the isolation of a MATa haploid strain R1918, with genotype hmg1::kanR; kanRtetO7-HMG2; URA3-CMVp-tTA*. This strain grew well on plates containing no doxycycline, and grew very poorly on plates containing 100 μg/ml doxycycline.

Construction of Yeast Strain R1446

Strain R1158, containing URA3-CMVp-tTA integrated at the ura3-0 locus, was constructed similarly to R1200. Strain R1446 was constructed by transforming R1158 with a PCR-amplified kanR-tetO7 fragment flanked with ERG11 homology such that, upon integrating at the ERG11 locus, replaced with 450 bp of sequence immediately upstream of the ERG11 start codon. This strain grew well in the absence of doxycycline, and grew very poorly on plates containing 1 μg/ml doxycycline.

Transcriptional State Measurement

PCR amplified products representing 6065 ORF's from the genome of S. cerevisiae were spotted onto polylysine treated microscope slides using an array robot. After printing, the arrays were processed to covalently bind the DNA to the polylysine coating, neutralize the reactivity of the unbound slide surface, and denature the bound strands of DNA. Processed arrays were hybridized with fluorescently labeled cDNA made by incorporating eith Cy3- or Cy5-dUTP during reverse transcription reactions of the RNA samples to be tested. Fluorescently labeled cDNA was hybridized to the arrays in 22 μl of hybridization solution (3× SSC, 0.75 μg/μl poly A DNA, 0.2% SDS) underneath a 22×30 mm glass cover slip at 63° C. for six hours. Arrays were then washed briefly in primary wash solution (1.5× SSC) and dried in a centrifuge before scanning.

Results

Drug responses for the yeast strains R1918 and R1446 were obtained by titrating cell cultures of each straing with graduated levels of doxycycline and measuring transcription levels as described above. The Tet promoter system used in both of these strains has been previously described (see, e.g., Gari et al., 1997, Yeast 13:837–848). This promoter is modulated by the concentration of the antibiotic tetracycline as well as by the structurally related compound doxycycline. Thus, in the absence of doxycycline, the promoter induces a high level of expression, and the addition of increasing levels of doxycycline causes increased repression of promoter activity. Intermediate levels of gene expression can be achieved in the steady state by addition of intermediate levels of drug. Furthermore, levels of doxycycline that give maximal repression of promoter activity (10 μg/ml) have no significant effect on the growth rate of wild type yeast cells (see Gari et al., supra). Thus, doxycycline has a single primary target in the above describe yeast strains: HMG2 (in yeast strain R1918), and ERG11 (in yeast strain R1446).

Figure 7:
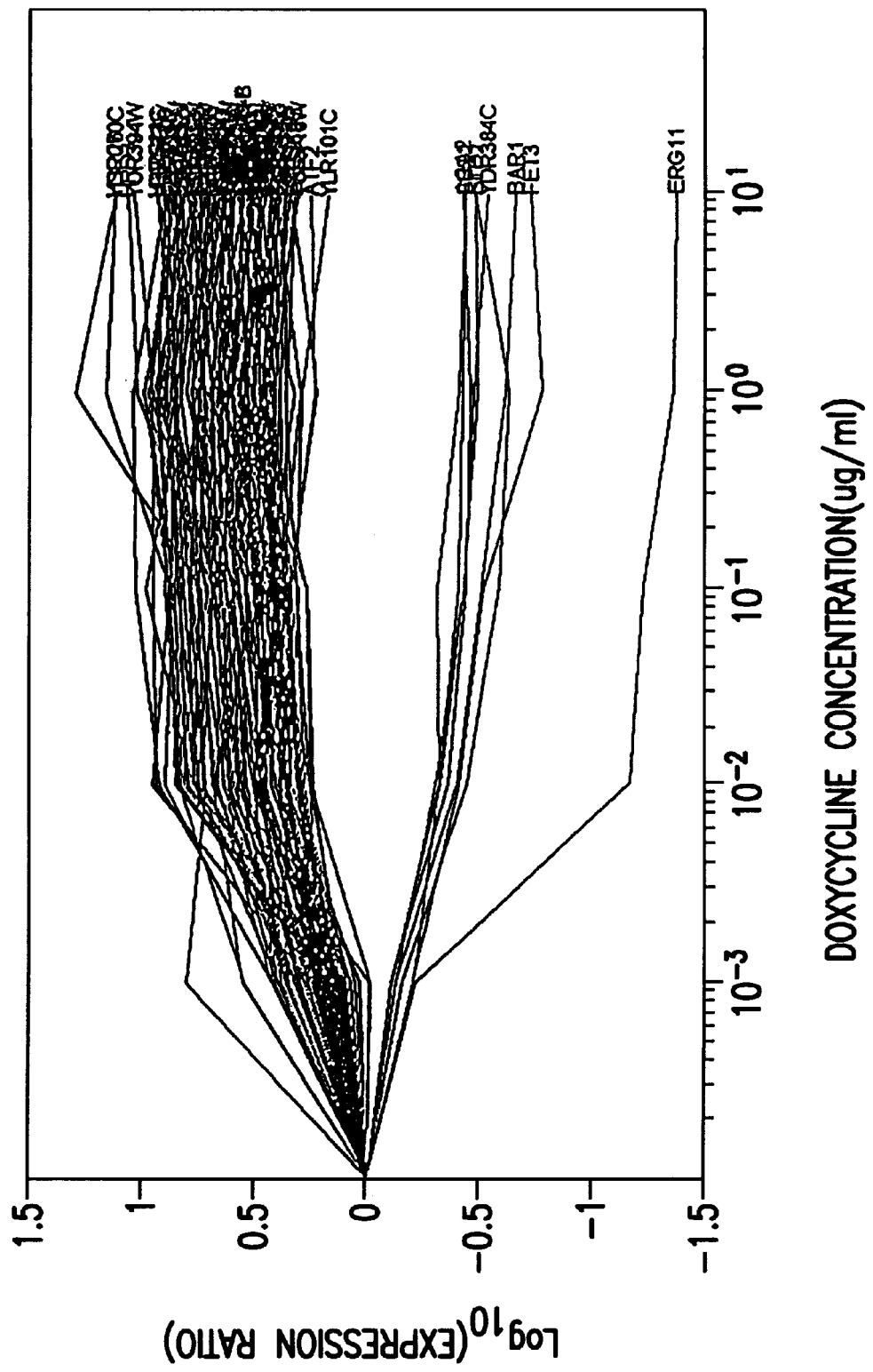
FIG. 7 illustrates the response data to controlled inhibition of ERG11 gene transcription in yeast strain R1446 containing a Tet-promoter construct under control of doxycycline; the transcriptional responses are therefore all mediated via a single primary target: ERG11 protein; the decrease in ERG11 transcription itself is shown by the lower curve.

FIG. 7 shows the drug response for those genes of strain R1446 that had the largest expression changes in response to doxycycline. The decrease in the ERG11 transcription itself is shown by the lower curve. Each of the drug responses shown in FIG. 7 was fit to a Hill function (Equation 2) and their inflection drug concentrations were determined from the fit parameter $x_0$. FIG. 8 shows the resulting histogram of inflection drug concentrations, excluding the response of the ERG11 transcript itself. As expected, the distribution of inflection drug concentrations is unimodal; the two peaks seen in the plot are statistical fluctuations in the inflection values from bin to bin, and are not statistically significant. Thus, the distribution is consistent with the biological knowledge that this experiment was a single-protein inhibition, i.e., had only one primary target.

Figure 9:
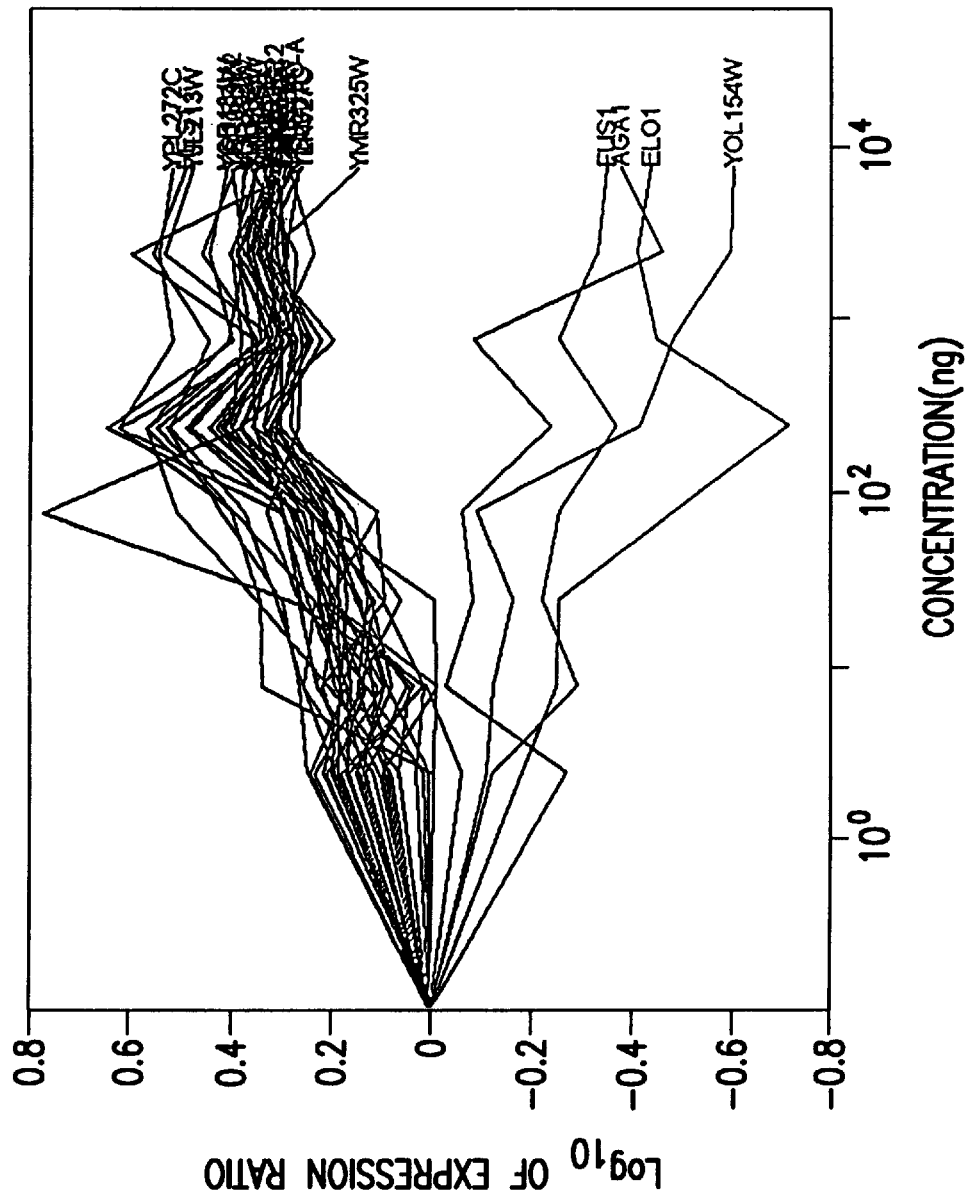
FIG. 9 illustrates the response data to controlled inhibition of HMG2 gene transcription in yeast strain R1918, containing tet-promoter construct under control of doxycycline; the transcriptional responses are all mediated via a single primary target: the HMG2 protein.
Figure 10:
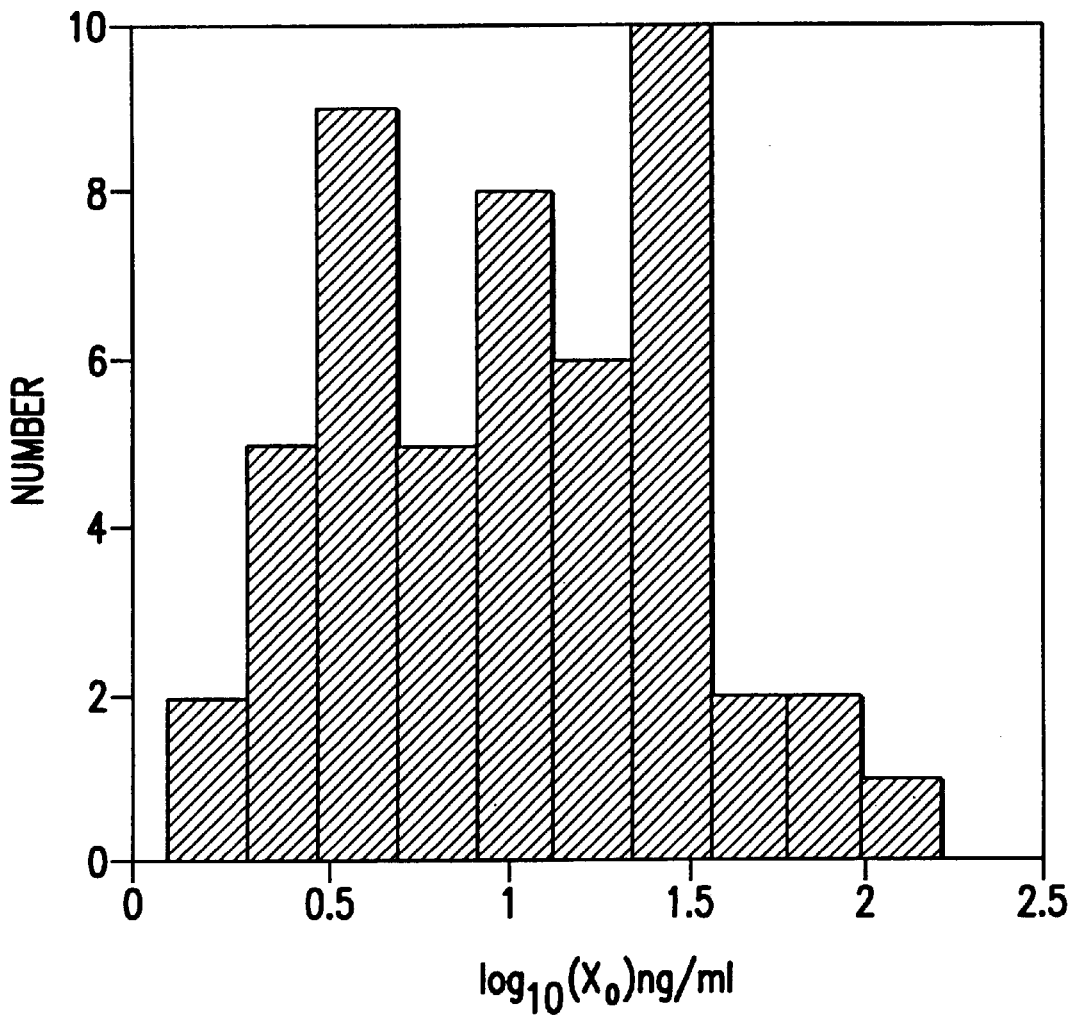
FIG. 10 illustrates the distribution of inflection concentrations $x_0$ obtained from fitting a Hill function to the drug response shown in FIG. 9.

FIG. 9 shows the drug response for those genes of strain R1918 that had the largest expression changes in response to doxycycline. The histogram of their inflection drug concentrations, excluding the response of the HMG2 transcript, is shown in FIG. 10. Again the distribution of $x_0$ is unimodal as expected for this activation of a single protein-mediated pathway.

6.3. Assessing the Confidence Level of Bimodality

This example illustrates the use of the statistical methods of the invention, described in Section 5.3.3 above, for evaluating a distribution of inflection drug concentrations to determine the number of modes of distribution. Specifically, the Fisher Distance FD was maximized and evaluated for each of the distribution of inflection drug concentration described in Sections 6.1 and 6.2 (FIGS. 6 and 8, respectively). The values of $FD_{max}$ obtained for each distribution were compared to distributions of $FD_{max}$ values for unimodal distribution, of various shapes, generated by Monte Carlo realizations of the "parent" distributions (i.e., the actual distribution data). The confidence level obtained for the histogram described in Section 6.1 (FIG. 6) is >99.9%, confirming that this distribution is indeed bimodal and that, consequently, the drug FK506 acts via two primary targets in yeast. By contrast, the confidence for bimodality in the histogram shown in FIG. 8 (Section 6.2) is only 30%. This result is consistent with the visual appearance of the histogram, and with the biological knowledge that the titration from which it was derived (FIG. 7) was a single-protein inhibition.

Figure 11:
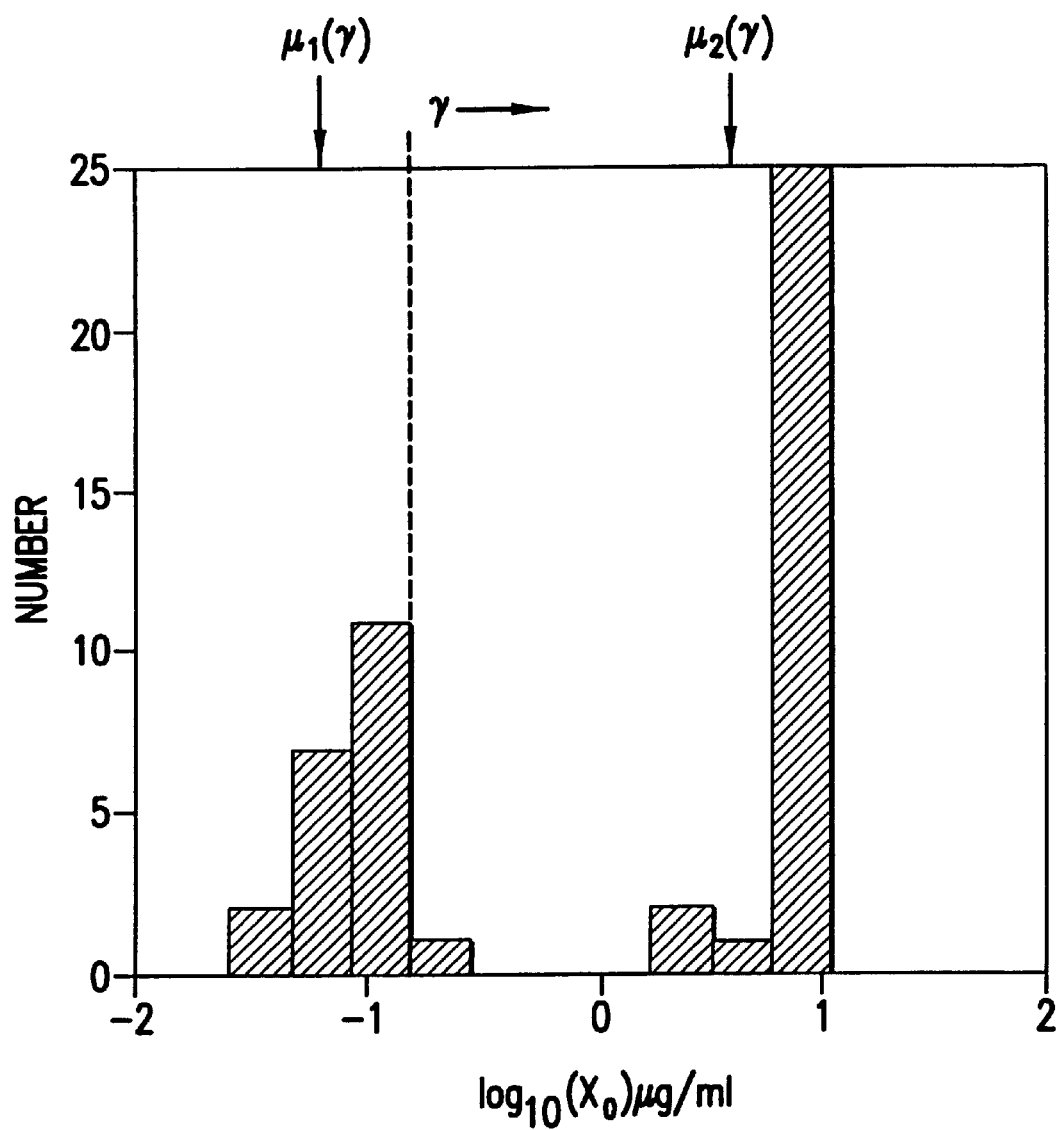
FIG. 11 shows the calculation of the Fisher Distance for the histogram shown in FIG. 6.

In more detail, FIG. 11 illustrates calculation of the Fisher Distance FD of the histogram shown in FIG. 6 as a function of the partition location γ. For each choice of a γ the mean and second moment was computed for the data of the left partition ($\mu_1$ and $\sigma_1$) and of the right partition ($\mu_2$ and $\sigma_2$). These separate values were then used to calculate FD according to Equation 4 in Section 5.3.3 above.

FIG. 12B plots FD vs. the partition location γ for the histogram in FIG. 6. The histogram itself is reproduced in FIG. 12A, with a vertical line marking the value of γ at which FD has a maximum. The maximum value $FD_{max}$, indicated in FIG. 12B by the vertical line, is 113.78. This value is much larger than the value of $FD_{max}$ expected from a unimodal distribution, and is, in itself, highly suggestive of a genuine bimodal distribution.

In order to assign a quantitative significance to the value of $FD_{max}$ obtained from the actual response data, its value was compared to distributions of $FD_{max}$ values empirically generated under the null hypothesis of unimodality. In more detail, histograms of $FD_{max}$ for unimodal uniform distribution, unimodal triangular distributions (i.e., ramping of left to right), and unimodal guassian distributions were generated with 1000 Monte Carlo realizations of the actual data done for 100 histogram elements in each realization, and binned with the same resolution as the actual data histogram of FIG. 6. The histogram of $FD_{max}$ values thus obtained for a unimodal uniform distribution is shown in FIG. 13A. The histogram of $FD_{max}$ values for the unimodal triangular distribution is shown in FIG. 13B. The two histograms are very similar despite the fact that they were generated for distributions of very different shapes. Results for the unimodal Guassian distribution (data not shown) were also very similar. Further, the Monte Carlo results for the unimodal distributions were also found to be insensitive to both the number of elements and the binning resolution (data not shown).

The probability value P that the observed $FD_{max}$ value actually came from a unimodal distribution was then assessed by determining the fraction of $FD_{max}$ values in FIG.

13A or 13B which are higher than the observed $F_{max}$, i.e., by evaluating the fraction of area in the histogram of FIG. 13A or 13B to the right of the observed $FD_{max}$. In particular, the uniform distribution of FIG. 13A was used to evaluate P since it is a somewhat broader distribution and thus leads to somewhat more conservative probability values. The resultant probability thus obtained for the data in FIGS. 12A–B is P<0.1%. Thus, the confidence level that the data is actually bimodal and not unimodal was determined to be 1−P>99.9%.

FIG. 14B plots the Fisher Distance FD vs. the partition location γ for the distribution of FIG. 8 from the specific ERG11 protein perturbation. The distribution itself is reproduced in FIG. 14A with a vertical line marking the value of γ at which FD has a maximum. In this case, $FD_{max}$<12 is much lower than the value of $FD_{max}$ determined above for the bimodal distribution from titration with FK506. The value of $FDM_{max}$ obtained for ERG11 protein perturbation was compared to a uniform unimodal distribution generated with Monte Carlo realizations of the actual data as described above. The confidence for bimodality was thereby determined to be only 30% (P=0.7). Thus, there is no statistical evidence for bimodality in this case.

Finally, the confidence for bimodality was also determined for the distribution of FIG. 10 from the specific HMG2 protein perturbation, according to the methods described above for FK506 and ERG11 specific perturbation. The confidence for bimodality in that histogram is only 10%, again consistent with the expectation for this single-protein perturbation.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appending claims, along with the full scope of equivalents to which such claims are entitled.

What is claimed is:

1. A method for determining the presence of a number of primary targets of a drug composition in a cell type, said method comprising determining the number of expression sets wherein:
   (a) the expression sets each comprise a plurality of cellular constituents having similar inflection concentrations of the drug composition;
   (b) the inflection concentration of the drug composition for a cellular constituent is the level of exposure to the drug composition at which the cellular constituent is increased or decreased by the drug composition in a drug response; and
   (c) the drug response comprises measured amounts of the pluralities of cellular constituents in a cell of the cell type at a plurality of levels of exposure of said cell type to the drug composition,
wherein each expression set indicates the presence of a different primary target of the drug composition in the cell type.

2. The method of claim 1, wherein the inflection concentration of the drug composition for the cellular constituent is the level of exposure to the drug composition at which the absolute slope of a plot of the measured amount of the cellular constituent in the drug response is maximum.

3. The method of claim 1, wherein the inflection concentration of the drug composition for the cellular constituent is the level of exposure to the drug composition at which the measured amount of the cellular constituent in the drug response is one-half of its asymptotic value.

4. The method of claim 1, wherein the measured amounts of cellular constituents in the drug response are interpolated.

5. The method of claim 4, wherein the measured amounts of cellular constituents in the drug response are interpolated by spline fitting.

6. The method of claim 4, wherein the measured amounts of cellular constituents in the drug response are interpolated by model fitting to a parameterized function.

7. The method of claim 6, wherein the parameterized function is a Hill function.

8. The method of claim 7, wherein the inflection concentration of a cellular constituent for the drug composition is the inflection point parameter of the Hill function.

9. The method of claim 1, wherein the expression sets are identified from a histogram of the inflection concentrations of the pluralities of cellular constituents, wherein each mode in the histogram identifies an expression set.

10. The method of claim 9, wherein the modes in the histogram are identified by visual inspection of the histogram.

11. The method of claim 9, wherein the modes in the histogram are identified by an objective statistical test.

12. The method of claim 11, wherein the objective statistical test is based on the Fisher Distance.

13. The method of claim 12, wherein the objective statistical test based on the Fisher Distance is used to test for bimodality of the histogram.

14. The method of claim 13, wherein the objective statistical test based on the Fisher Distance comprises determining the maximum Fisher Distance of the histogram, wherein value of the maximum Fisher Distance positively correlate with the levels of confidence that the histogram is bimodal.

15. The method of claim 14, wherein the objective statistical test based on the Fisher Distance further comprises determining a confidence level for bimodality of the histogram, the confidence level being determined by a method comprising comparing the determined maximum Fisher Distance of the histogram to an empirical distribution of maximum Fisher Distance values for a hypothesis of unimodality.

16. The method of claim 15, wherein the empirical distribution of maximum Fisher Distance values is a uniform distribution.

17. The method of claim 15, wherein the empirical distribution of maximum Fisher Distance values is a triangular distribution.

18. The method of claim 15, wherein the empirical distribution of maximum Fisher Distance values is a Guassian distribution.

19. The method of claim 15, wherein the confidence level for bimodality of the histogram is further determined from the probability that the determined maximum Fisher Distance of the histogram is from a unimodal distribution.

20. The method of claim 19, wherein the probability is the fraction of the empirical distribution of maximum Fisher Distance values having values greater than the determined maximum Fisher Distance.

21. The method of claim 19 or 20, wherein the confidence level for bimodality of the histogram is the probability that the determined maximum Fisher Distance of the histogram is from a unimodal distribution subtracted from unity.

22. The method of claim 12, wherein the objective statistical test based on the Fisher Distance is used to test for levels of multimodality greater than bimodality.

23. The method of claim 22, wherein the objective statistical test based on the Fisher Distance comprises:

(a) dividing the histogram into subintervals suspected of containing two modes; and (b) testing the subinterval of the histogram for bimodality.

24. The method of claim 1, wherein the cellular constituents comprise abundances of a plurality of RNA species.

25. The method of claim 24, wherein the measured amounts of the pluralities of cellular constituents in a cell of the cell type are obtained by a method comprising contacting one or more gene transcript arrays (i) with RNA, or with cDNA derived therefrom, from a cell of the cell type that is exposed to the levels of exposure to the drug composition, and (ii) with RNA, or with cDNA derived therefrom, from a cell of the cell type that is not exposed to the levels of exposure to the drug composition.

26. The method of claim 1, wherein the cellular constituents comprise abundances of a plurality of protein species.

27. The method of claim 26, wherein the measured amounts of the abundances of the plurality of protein species are obtained by a method comprising contacting an antibody array with proteins from a cell of the cell type, wherein the antibody array comprises a surface with attached antibodies, the antibodies being capable of binding with the plurality of protein species.

28. The method of claim 26, wherein the measured amounts of the abundances of the plurality of protein species are obtained by a method comprising performing two-dimensional electrophoresis of proteins from a cell of the cell type.

29. The method of claim 1, wherein the cellular constituents comprise activities of a plurality of protein species present in the cell type.

30. A method for determining the presence of a number of primary targets of a drug composition in a cell type, said method comprising:

(a) providing a drug response, said drug response comprising measured amounts of a plurality of cellular constituents in a cell of the cell type at a plurality of levels of exposure of said cell type to the drug composition, by a method comprising measuring said plurality of cellular constituents in a cell of the cell type at a plurality of levels of exposure of said cell type to the drug composition;

(b) determining an inflection concentration of the drug composition for each cellular constituent in the plurality of cellular constituents, the inflection concentration of the drug composition for a cellular constituent in the plurality of cellular constituents being the level of exposure to the drug composition at which the cellular constituent is increased or decreased in the drug response; and (c) determining the number of expression sets of cellular constituents, each expression set comprising those cellular constituents with similar inflection concentrations for the drug composition, wherein each expression set indicates the presence of a different primary target of the drug composition in the cell type.

31. A method for determining the presence of a number of primary targets of a change in physical environment of a cell type, said method comprising determining a number of expression sets wherein:

(a) the expression sets each comprise a plurality of cellular constituents, each cellular constituent in a single expression set having a similar inflection concentration for the change in physical environment;

(b) the inflection concentration of the change in physical environment for a cellular constituent is the level of the change in physical environment at which the cellular constituent is increased or decreased by the change in physical environment in a response profile; and (c) the response profile comprises measured amounts of the pluralities of cellular constituents in a cell of the cell type at a plurality of levels of the change in physical environment, wherein each expression set indicates the presence of a different primary target of the change in physical environment.

* * * * *

UNITED STATES PATENT AND TRADEMARK OFFICE
CERTIFICATE OF CORRECTION

PATENT NO. : 6,146,830
DATED : November 14, 2000
INVENTOR(S) : Stephen H. Friend and Roland Stoughton It is certified that error appears in the above-identified patent and that said Letters Patent is hereby corrected as shown below:

Claim 1,
Line 3, after "...comprising determining," delete "the" and insert -- a --.

Signed and Sealed this

Twenty-eighth Day of August, 2001

*Attest:*

NICHOLAS P. GODICI
*Attesting Officer*     *Acting Director of the United States Patent and Trademark Office*